(12) United States Patent
Davison et al.

(10) Patent No.: US 12,316,704 B2
(45) Date of Patent: *May 27, 2025

(54) MULTIPLEXING OF DEDICATED COMMUNICATION CHANNELS FOR MULTIPLE ENTITIES

(71) Applicant: CommuniCare Technology, Inc., Bozeman, MT (US)

(72) Inventors: Lucien L. Davison, Bozeman, MT (US); Duane Wes Hunt, Bozeman, MT (US); James T. Woodson, Bozeman, MT (US); Erich H. Hannan, Bozeman, MT (US)

(73) Assignee: CommuniCare Technology, Inc., Bozeman, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/586,028

(22) Filed: Feb. 23, 2024

(65) Prior Publication Data

US 2024/0195869 A1 Jun. 13, 2024

Related U.S. Application Data

(63) Continuation of application No. 18/186,806, filed on Mar. 20, 2023, now Pat. No. 11,936,727, which is a
(Continued)

(51) Int. Cl.
*H04L 67/1095* (2022.01)
*H04L 67/60* (2022.01)

(52) U.S. Cl.
CPC .......... *H04L 67/1095* (2013.01); *H04L 67/60* (2022.05)

(58) Field of Classification Search
CPC .. G06F 3/0482; G06F 16/951; G06F 16/9535; G06F 21/6245; G06F 3/04;
(Continued)

(56) References Cited

U.S. PATENT DOCUMENTS 6,665,647 B1 12/2003 Haudenschild
7,630,986 B1 12/2009 Herz
(Continued)

FOREIGN PATENT DOCUMENTS

EP 2778922 9/2014

OTHER PUBLICATIONS

International Search Report and Written Opinion for PCT Patent Application No. PCT/US2020/029380, mailed Jul. 1, 2020; 17 pages.
(Continued)

*Primary Examiner* — Brian J. Gillis
*Assistant Examiner* — Thao D Duong
(74) *Attorney, Agent, or Firm* — McDermott Will & Emery LLP

(57) ABSTRACT

Systems and methods for multiplexing of a dedicated communication channel for multiple entities, including initiating, at a first entity, a request to share data with a second entity; sharing a portion of an aggregate record for the with the second entity including creating an entity-specific copy; initiating, at the first entity, a request to share data with a third entity; and sharing a portion of the aggregate record with the third entity including creating an entity-specific copy. The portions shared with the second and third entities are dependent on data sharing rules defining shared data, linked data, and entity-specific data that is i) nonsynchronous and ii) provided for display only at the entity associated with the data.

17 Claims, 18 Drawing Sheets

Related U.S. Application Data continuation of application No. 17/529,965, filed on Nov. 18, 2021, now Pat. No. 11,616,836, which is a continuation of application No. 17/339,430, filed on Jun. 4, 2021, now Pat. No. 11,212,346, which is a continuation of application No. 16/399,417, filed on Apr. 30, 2019, now abandoned.

(58) Field of Classification Search
CPC ..... G06F 16/2282; G06F 16/02; G06N 20/00; G06N 7/005; G06N 3/0454; H04L 2209/38; H04L 41/0893; H04L 67/306; H04L 63/0428; H04L 67/1097
See application file for complete search history.

(56) References Cited

U.S. PATENT DOCUMENTS

| | | | |
|---|---|---|---|
| 8,510,126 B2 | 8/2013 | Martin | |
| 8,521,564 B1 | 8/2013 | Ciechanowski | |
| 8,566,115 B2 | 10/2013 | Moore | |
| 8,630,870 B2 | 1/2014 | Hussam | |
| 9,058,635 B1 | 6/2015 | Rybkin | |
| 9,633,404 B2 | 4/2017 | Chawla | |
| 9,904,766 B2 | 2/2018 | Chawla | |
| 9,973,484 B2 | 5/2018 | Reid | |
| 10,169,607 B1 * | 1/2019 | Sheth | G16H 15/00 |
| 10,270,865 B1 * | 4/2019 | Heath | H04L 67/146 |
| 10,332,625 B2 | 6/2019 | Ting | |
| 10,395,772 B1 | 8/2019 | Lucas | |
| 10,438,694 B2 | 10/2019 | Napora | |
| 10,542,004 B1 | 1/2020 | Perez | |
| 10,607,468 B2 * | 3/2020 | Cullin | G08B 25/006 |
| 10,726,152 B1 * | 7/2020 | Durham | H04L 63/10 |
| 10,740,547 B2 * | 8/2020 | Malek | G06F 3/0484 |
| 10,790,050 B2 | 9/2020 | Fierer | |
| 11,348,681 B1 | 5/2022 | Morrow | |
| 2001/0016822 A1 | 8/2001 | Bessette | |
| 2005/0187794 A1 | 8/2005 | Kimak | |
| 2010/0241595 A1 | 9/2010 | Felsher | |
| 2013/0018671 A1 | 1/2013 | Hussann | |
| 2013/0318347 A1 | 11/2013 | Moffat | |
| 2013/0332987 A1 | 12/2013 | Tenneti | |
| 2014/0214709 A1 | 7/2014 | Greaney | |
| 2014/0223099 A1 | 8/2014 | Kidron | |
| 2015/0154357 A1 | 6/2015 | Biswas et al. | |
| 2016/0277374 A1 | 9/2016 | Reid | |
| 2016/0291940 A1 | 10/2016 | Searle et al. | |
| 2017/0048323 A1 | 2/2017 | Schlapfer | |
| 2017/0161439 A1 | 6/2017 | Raduchel | |
| 2017/0315683 A1 | 11/2017 | Boucher et al. | |
| 2018/0039737 A1 | 2/2018 | Dempers | |
| 2020/0350082 A1 * | 11/2020 | Davison | G16H 80/00 |
| 2021/0182111 A1 | 6/2021 | Jakobsson | |
| 2023/0130914 A1 | 4/2023 | Kaliraman | |
| 2023/0153539 A1 * | 5/2023 | Uhl | G16H 80/00 705/2 |

OTHER PUBLICATIONS

Coiera, Enrico. 2006. "Communication systems in healthcare". Clin Biochem Rev. 27(2): 89-98. all pages. https:// www.ncbi.nlnn.nih.gov/pnnc/articles/PMC1579411/ (Year: 2006).

El Emam K, Rodgers S, Malin B. "Anonymising and sharing individual patient data". BMJ. 2015. 350: h1139. all pages. Published Mar. 20, 2015. doi:10.1136/bmj.h1139 (Year: 2015).

Gordon, William J. 2018. "Blockchain Technology for Healthcare: Facilitating the Transition to Patient-Driven Interoperability". J Comp and Struct Biotech. vol. 16, pp. 224-230. all pages. https://doi.org/10.1016/j.csbj.2018.06.003 (Year: 2018).

(N.a.) 2017. "Patient Handoffs: The Gap Where Mistakes Are Made". PSQH. all pages. https://www.psqh.conn/analysis/ patient-handoffs-gap-nnistakes-nnade/#:-:text=A%20patient%20handoff%20(also%20known,the%20provider%20taking%20the%20patient). (Year: 2017).

(N.a.) 2018. "Physician Sign Out: The Patient Hand-Off App". all pages. http://web.archive.org/web/20180612123506/https:// www.physiciansignout.com/ (Year: 2018).

Haras, Consuela et al. 2005. "Patient Data Synchronization Process in a Continuity of Care Environment". AMIA Annu Symp Proc. 2005:296-300. all pages. https://www.ncbi.nlnn.nih.gov/pnnc/articles/PMC1560702/ (Year: 2005).

(N.a.) 2012. "Healthcare Provider Tool Kit: Global Data Synchronization Network (R) (GDSN (R))". all pages. https://www.gs1us.org/ DesktopModules/Bring2nnind/DMX/Download.aspx?Connnnand-CoreDownload&Entryld-636&language=en-US&Portal ld=0&Tabld=134 (Year: 2012).

* cited by examiner

MULTIPLEXING OF DEDICATED COMMUNICATION CHANNELS FOR MULTIPLE ENTITIES

RELATED APPLICATION

This application is a Continuation Applications of U.S. patent application Ser. No. 18/186,806 filed Mar. 20, 2023, which is a Continuation Applications of U.S. patent application Ser. No. 17/529,965 filed Nov. 18, 2021, now U.S. Pat. No. 11,616,836, which is a Continuation Applications of U.S. patent application Ser. No. 17/339,430 filed Jun. 4, 2021, now U.S. Pat. No. 11,212,346, which is a Continuation Applications of U.S. patent application Ser. No. 16/399,417 filed Apr. 30, 2019, now abandoned, the contents of which are incorporated herein by reference in their entirety.

FIELD OF THE DISCLOSURE

This disclosure relates generally to systems and methods for exchanging data between entities using dedicated communication channels.

SUMMARY

Innovative aspects of the subject matter described in this specification may be embodied in a system for exchanging information between entities, including an inter-facility communication platform; a plurality of client computing devices, each configured to be operated at a respective one of three or more entities; a data store comprising an aggregate record associated with a particular individual, the aggregate record including: demographic data for the particular individual; entity-owned data associated with the particular individual; and data representing information sharing requests exchanged between the three or more entities associated with the particular individual; and a rules data store comprising sharing rules defining: shared data in the aggregate record that is automatically synchronized between the three or more entities when added or modified at one of the three or more entities; linked data in the aggregate record that is i) nonsynchronous between the three or more entities, and ii) provided for display at the three or more entities independent of the one of the three or more entities at which the linked data was added or modified in the aggregate record; and entity-specific data that is i) nonsynchronous between the three or more entities and ii) provided for display only at the entity that is associated with the entity-specific data; wherein the communication platform is configured to: i) establish a dedicated communication channel over which the three or more entities exchange data associated with the particular individual; ii) detect a first request from a first one of the plurality of client computing devices at a first one of the three or more entities to share data associated with the particular individual with a second one of the three of more entities over the dedicated communication channel; iii) in response to detecting the first request, share a first portion of the aggregate record associated with the particular individual with a second one of the plurality of client computing devices at the second healthcare entity, wherein the first portion of the aggregate record shared is dependent on the data sharing rules; iv) detect a second request from a client computing device at the first healthcare entity to share data associated with the particular individual with a third one of the three of more entities over the dedicated communication channel; and v) in response to detecting the second request, share a second portion of the aggregate record associated with the particular individual with a third one of the plurality of client computing devices at the third entity, wherein the second portion of the aggregate record shared is dependent on the data sharing rules.

Other embodiments of these aspects include corresponding systems, apparatus, and computer programs, configured to perform the actions of the methods, encoded on computer storage devices.

BRIEF DESCRIPTION OF THE DRAWINGS

For a more complete understanding of the present invention and its features and advantages, reference is now made to the following description, taken in conjunction with the accompanying drawings, in which.

DESCRIPTION OF PARTICULAR EMBODIMENT(S)

Figure 1:
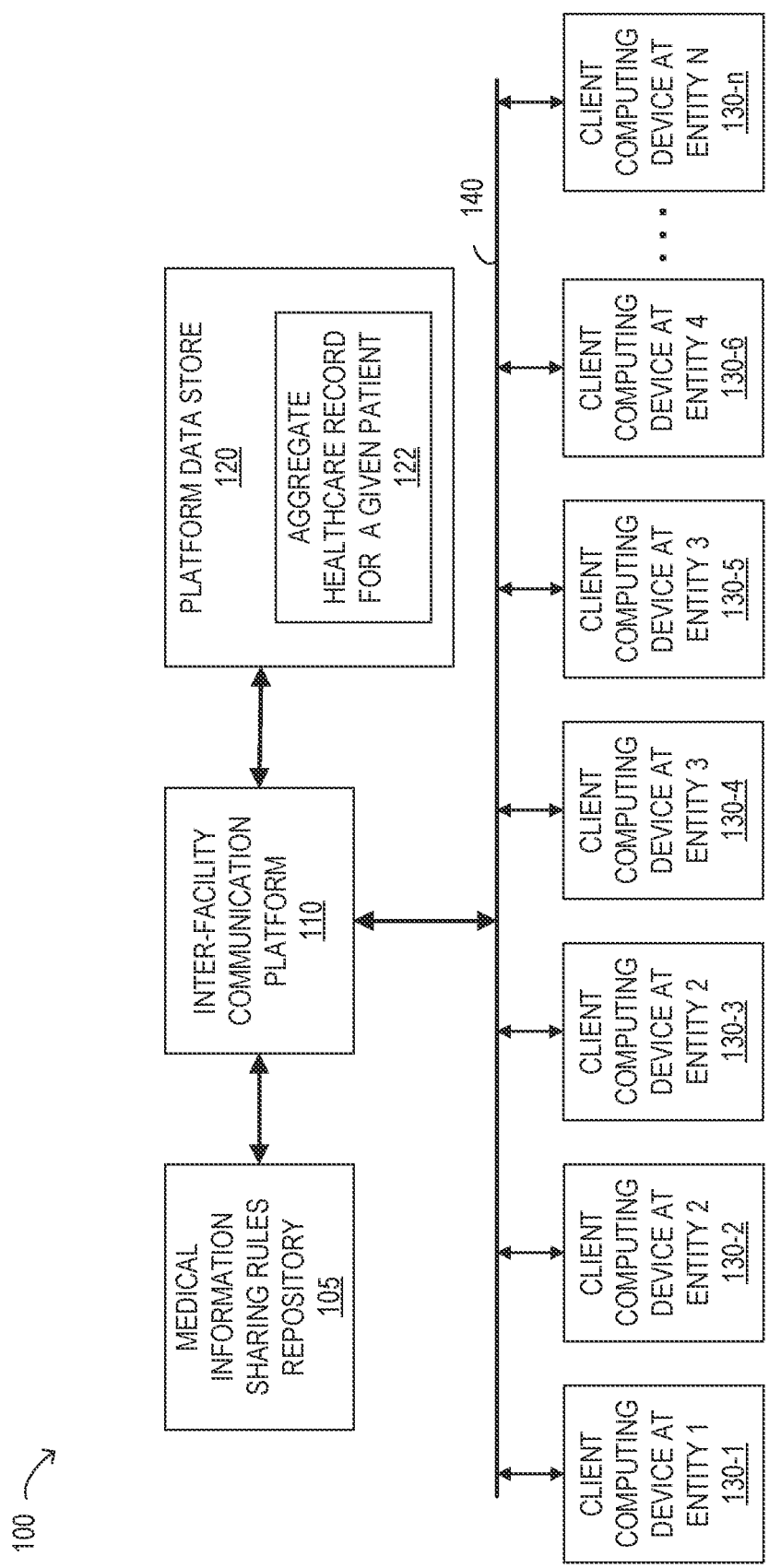
FIG. 1 is a block diagram illustrating selected elements of a system for exchanging information between entities using dedicated communication channels, according to some embodiments.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As noted above, medical informatics solutions include providing methods, resources, and devices to facilitate the care of patients by doctors and nurses whose needs include the acquisition, storage, retrieval, and use of information associated with their patients. Some existing medical informatics systems allow patient information to be shared between users at two healthcare entities in a fixed pair of healthcare entities. However, sharing and synchronizing patient information between more than two facilities, while complying with patient data protection regulations, is difficult.

As will be described in further detail, the systems and methods disclosed herein may implement the rules-based inter-facility exchange of medical information between healthcare entities using dedicated communication channels per patient. These systems and methods may be applied to exchange medical information between any number of healthcare entities that are added to a dedicated communication for a given patient. The dedicated patient communication channel may be associated with an aggregate healthcare record in a data store, entity-specific copies of which are owned by respective ones of the healthcare entities that are active on the dedicated patient communication channel. The aggregate healthcare record may include demographic data for the given patient, entity-owned data associated with the given patient, and data representing information sharing requests exchanged between multiple healthcare entities on behalf of the given patient.

The respective portions of the aggregate healthcare record included in each of the entity-specific copies may be dependent on medical information sharing rules defining shared information in the aggregate healthcare record that is automatically synchronized between multiple healthcare entities when added or modified by a user at one of the healthcare entities, linked information in the aggregate healthcare record that is not synchronized between healthcare entities but is visible to users at multiple healthcare entities regardless of the one of the healthcare entities at which it was added or modified in the aggregate healthcare record, and entity-specific information that is neither synchronized between healthcare entities nor visible to users at a healthcare entity other than a healthcare entity that owns the entity-specific information. In some embodiments, this private entity-owned information may reside behind a firewall at the healthcare entity that owns it.

For example, the medical information sharing rules may specify that demographic data included in the entity-specific copy of the aggregate healthcare record for a first healthcare entity is copied to a newly created entity-specific copy for a second healthcare entity in response to an information sharing request originating at the first healthcare entity and targeting the second healthcare entity. Furthermore, demographic data that is added to or modified in an entity-specific copy of the aggregate healthcare record for a first healthcare entity may be automatically synchronized, in real time, with demographic data in entity-specific copies of the aggregate healthcare record for other healthcare entities. In some embodiments, adding or modifying other types of data in an entity-specific copy of the aggregate healthcare record for a first healthcare entity may result in a synchronization with other entity-specific copies. In some embodiments, data other than demographic data that is added to or modified in an entity-specific copy of the aggregate healthcare record for a first healthcare entity may not be included in the data copied to a new entity-specific copy of the aggregate healthcare record for another healthcare entity using a copy-on-request operation. However, this information may be linked to and visible by all of the active healthcare entities on the dedicated patient communication channel Particular embodiments are best understood by reference to FIGS. 1, 2, 3A-3D, 4A-4F, 5A-5H, 6, 7, 8, 9, 10A-10D, and 11.

Turning now to the drawings, FIG. 1 is a block diagram illustrating selected elements of a system 100 for exchanging medical information between healthcare entities using dedicated patient communication channels, according to some embodiments. In the illustrated embodiment, system 100 includes an inter-facility communication platform 110, multiple client computing devices 130 each associated with a respective one of multiple healthcare entities, a medical information sharing rules repository 105, and a platform data store 120 including an aggregate healthcare record 122 for a given patient. For example, client computing device 130-1 is associated with an entity 1, client computing devices 130-2 and 130-3 are associated with an entity 2, client computing devices 130-4 and 130-5 are associated with an entity 3, client computing device 130-6 is associated with an entity 4, and client computing device 130-n is associated with an entity N. In other embodiments, the system may include a different number of client computing devices 130 associated with, or residing at, a different number of healthcare entities than shown in FIG. 1. In at least some embodiments, users at various healthcare entities who participate in the communication channel may generate data, including messages (e.g., text messages), images, audio or video clips, vital signs, lab results, the assignment of people to the patient communication channel, information sharing request logs, and activity logs.

In various embodiments, the client computing devices 130 may include a mobile device, such as a notebook computer, media player, personal data assistant, digital camera, cellular phone, smart phone, or tablet computer, or a mainframe computer or desktop computer. In various embodiments, a user at a healthcare entity may log into an application operating on a client computing device 130 and interacting with inter-facility communication platform 110 as a healthcare provider, such as a first responder, an emergency medical technician (EMT), a doctor, a nurse, or a lab technician, for example, who provides healthcare services to a given patient, or as an administrator authorized to add or modify configuration information, such as medical information sharing rules stored in medical information storing rules repository 105.

In various embodiments, medical information sharing rules repository 105 may reside on inter-facility communication platform 110 hardware or may be remote storage, such as cloud-based storage. Similarly, medical platform data store 120 may reside on inter-facility communication platform 110 hardware or may be remote storage, such as cloud-based storage, in different embodiments.

In at least some embodiments, aggregate healthcare record 122 may include, at various times, demographic data for the given patient, entity-owned data associated with the given patient, and/or data representing information sharing requests exchanged between client computing devices 130 associated with various healthcare entities on behalf of the given patient, among other information. The demographic data may include, for example, the patient's first name, last name, birth date, age, or gender, or contact information for the patient, a spouse or other family member, or a witness to an accident or to the onset of an illness, in various embodiments.

In at least some embodiments, medical information sharing rules repository 105 may include medical information sharing rules defining which, if any, elements in the aggregate healthcare record 122 represent shared information that is automatically synchronized between the client computing devices 130 associated with different healthcare entities when added or modified by a user at one of the healthcare entities. The medical information sharing rules may also define which, if any, elements in the aggregate healthcare record 122 represent linked information that is not synchronized between the client computing devices 130 associated with different healthcare entities but is visible to users of client computing devices associated with the different healthcare entities regardless of the one of the healthcare entities at which it was added or modified in the aggregate healthcare record 122. Furthermore, the medical information sharing rules may define which, if any, elements in the aggregate healthcare record 122 represent entity-specific information that is neither synchronized between the client computing devices 130 associated with different healthcare entities nor visible to users of client computing devices associated with a healthcare entity other than a healthcare entity that owns the entity-specific information.

In the example embodiment illustrated in FIG. 1, the inter-facility communication platform 110 establishes a dedicated communication channel 140 for the given patient over which medical information associated with the given patient is exchanged between healthcare entities 130 that provide services to, or on behalf of, the given patient. More specifically, when an information sharing request is submitted to the inter-facility communication platform 110 by one of the client computing devices 130 at a particular healthcare entity, the inter-facility communication platform 110 determines, based on information sharing rules that define what portion, if any, of the aggregate healthcare record 122 should be shared with the specified recipient at another healthcare entity.

In the example system illustrated in FIG. 1, the term "entity" may refer to any of a variety of healthcare facilities that receive patients, such as a hospital, a nursing home, a rehabilitation facility, an assisted living facility, a freestanding emergency room, an urgent care facility, a surgical center, a lab, an imaging center, or a doctor's office, or may refer to a transporting entity, such as an emergency medical services (EMS) agency, an ambulance service, a medical evacuation agency, or a medical helicopter transportation service.

In at least some embodiments, a dedicated communication channel for a given patient may be implemented using a particular combination of a relational database, an application tier, a worker tier, and push notifications. For example, in some embodiments, the relational database may be a commercial database cluster that provides high availability. Each dedicated patient communication channel may be made up of a collection of records in the database that are linked together through primary key and foreign key relationships. For each healthcare entity involved in the patient communication channel, there may be a database row record for their entity-specific copy of the aggregate healthcare record for the given patient. The database row records for each of the healthcare entities involved in the patient communication channel may be kept in synchronization with each other during active patient care in accordance with predefined medical information sharing rules applicable to the particular healthcare entities and the inter-entity relationships between them. All of the information added to the patient communication channel by users at a particular healthcare entity may be stored underneath their entity-specific copy of the aggregate healthcare record for the given patient. This may allow the entity-specific data that is owned by the particular healthcare entity to be virtually segregated at the data storage level. In at least some embodiments, the database row records for multiple entity-specific copies of the aggregate healthcare record may be linked together, which may allow for the generation of a view into all the data in the patient communication channel by assembling all of the corresponding parts of each constituent portion of the patient communication channel into a single, unified view.

In some embodiments, the systems described herein for exchanging medical information between healthcare entities using dedicated patient communication channels may include mobile and web-based applications that post data to an application programming interface (API) provided by an application tier that handles all of the data processing, business rules, and data storage requests. The API application tier may write jobs to a queue system and a worker tier may spawn independent threads that read from the queue to asynchronously process those jobs.

In some embodiments, the systems described herein for exchanging medical information between healthcare entities using dedicated patient communication channels may use push notifications to manage communication tasks on the patient communication channels. For example, a push notification may be implemented as a message or an alert that is received in the notification center of a mobile device, or in web browser. In some embodiments, workers processing communication jobs may pick up a request for communication and ultimately connect to a back-end system of the mobile device or web browser to send push notifications. In some embodiments and at particular times, based on the current state of the system, a specific customer configuration, the status of a given patient communication channel, and/or the state of a user of the mobile device or web browser, a worker may suppress sending a push notification or other message.

In some embodiments, a dedicated communication channel for a given patient may be implemented using technologies or combinations of technologies other than those described above. For example, a dedicated patient communication channel may be implemented using a data storage system other than a relational database to implement similar functionality. In some embodiments, class data storage systems that classify into Key-value, Document store, Graph, In-memory, or Search optimized systems may also be able to provide the high availability and fast response times suitable for implementing the dedicated patient communication channels described herein.

In still other embodiments, a dedicated communication channel for a given patient may be implemented using the WebSocket communication protocol. This communication protocol provides full-duplex communication channels over a single Transmission Control Protocol (TCP) connection. For example, in some embodiments, the WebSocket protocol may be used for sending real-time updates from a server back-end, such as a server that implements an inter-facility communication platform, directly to real-time applications for interacting with the server that are executing on various client computing devices.

Figure 2:
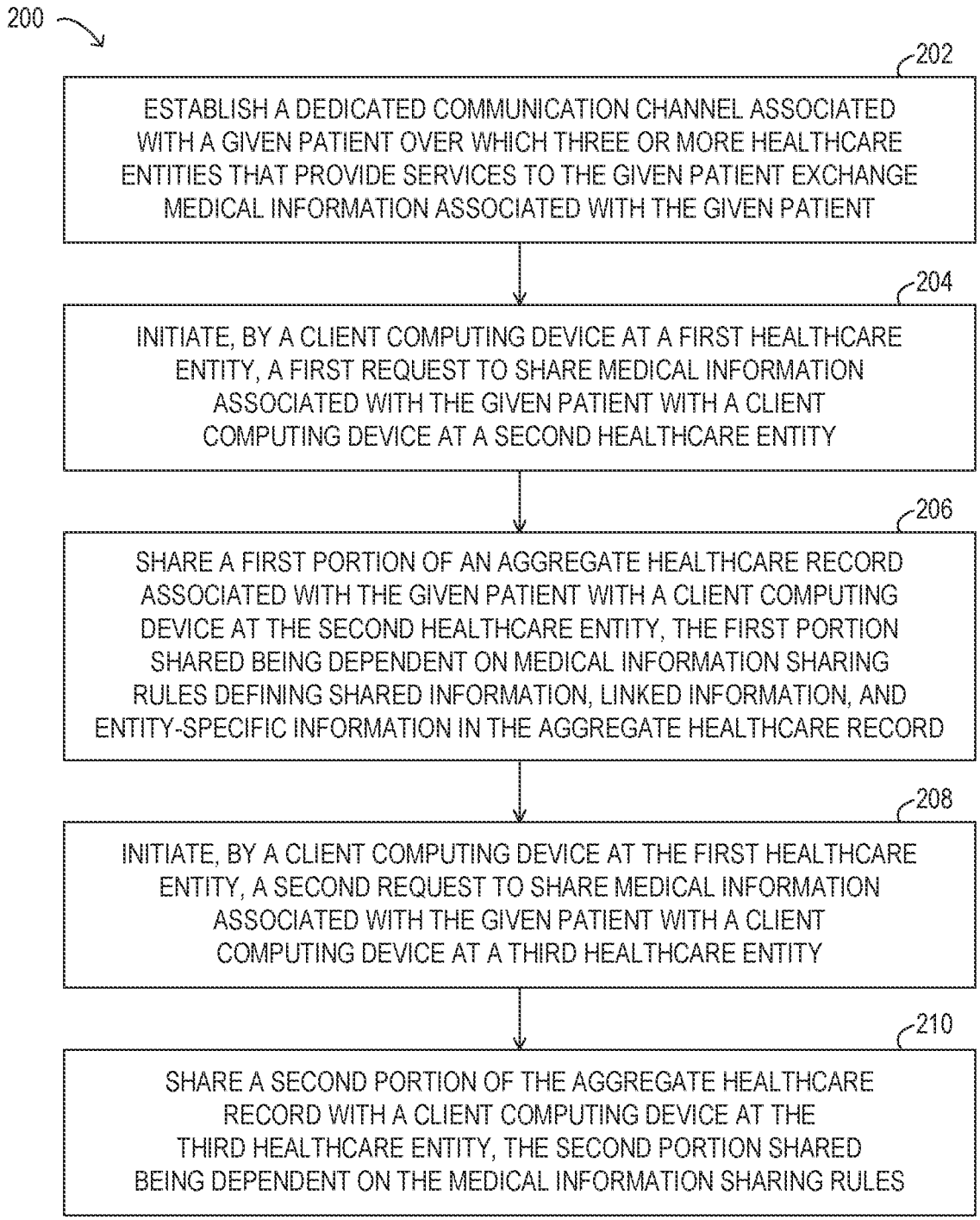
FIG. 2 is flow diagram illustrating selected elements of an embodiment of a method for exchanging information between entities using dedicated communication channels, according to some embodiments.

FIG. 2 is flow diagram illustrating selected elements of an embodiment of a method 200 for exchanging medical information between healthcare entities using dedicated patient communication channels, according to some embodiments. In various embodiments, operations of method 200 may be performed by an inter-facility communication platform such as inter-facility communication platform 110 illustrated in FIG. 1, in conjunction with multiple client computing devices, such as client computing devices 130 illustrated in FIG. 1. Method 200 may be performed once or repeatedly to exchange medical information between healthcare entities using dedicated patient communication channels. It is noted that certain operations described in method 200 may be optional or may be rearranged in different embodiments.

As illustrated in FIG. 2, method 200 may include, at 202, establishing a dedicated communication channel associated with a given patient over which three or more healthcare entities that provide services to the given patient exchange medical information associated with the given patient.

At 204, method 200 may include initiating, by a client computing device at a first healthcare entity, a first request to share medical information associated with the given patient with a client computing device at a second healthcare entity. In various embodiments, the information sharing request may be an information-only type sharing request, such as a request for a consult, or a patient handoff type request, such as a request to transfer or transport the given patient.

At 206, the method may include sharing a first portion of an aggregate healthcare record associated with the given patient with a client computing device at the second healthcare entity, The aggregate healthcare record may include demographic data for the given patient, entity-owned data associated with the given patient, and/or data representing information sharing requests exchanged between the three or more entities on behalf of the given patient. The first portion of the aggregate healthcare record shared may be dependent on medical information sharing rules defining shared information, linked information, and entity-specific information in the aggregate healthcare record.

At 208, method 200 may include initiating, by a client computing device at the first healthcare entity, a second request to share medical information associated with the given patient with a client computing device at a third healthcare entity. Here again, the information sharing request may be an information-only type sharing request, such as a request for a consult, or a patient handoff type request, such as a request to transfer or transport the given patient.

At 210, the method may include sharing a second portion of the aggregate healthcare record with a client computing device at the third healthcare entity. The second portion of the aggregate healthcare record shared may be dependent on the medical information sharing rules.

As will be described in more detail below, in at least some embodiments of the present disclosure, decisions about what medical information added to an aggregate healthcare record for a given patient by one healthcare entity should be shared with other healthcare entities, and under what circumstances, may be dependent on predefined medical information sharing rules, sure as those stored in medical information sharing rules repository 105 illustrated in FIG. 1. For example, the medical information sharing rules may specify which data elements in an aggregate healthcare record represent shared information that is automatically synchronized between healthcare entities, linked information that is not synchronized between healthcare entities but is visible to users at multiple healthcare entities, and entity-specific information that is neither synchronized between the healthcare entities nor visible to users at a healthcare entity other than a healthcare entity that owns the entity-specific information.

Table 1, shown below, illustrates an example collection of medical information sharing rules.

TABLE 1

Example medical information sharing rules

| Data Element | Copy on Request | Synchronize on Client Devices | Synchronize at Admin | View in Table |
|---|---|---|---|---|
| Patient Demographic Data | | | | |
| Patient name | YES | YES | NO | NO |
| Date of birth | YES | YES | NO | NO |
| Age | YES | YES | NO | NO |
| Gender | YES | YES | NO | NO |
| Height | YES | YES | NO | NO |
| Weight | YES | YES | NO | NO |
| Common Case Elements | | | | |
| Room | NO | NO | NO | YES |
| Hospital | NO | NO | NO | YES |
| Method of arrival | NO | NO | NO | YES |
| Status (active/stopped) | YES | YES | N/A | N/A |
| Additional Patient Related Elements | | | | |
| Images | LINKED | LINKED | LINKED | NO |
| Patient contacts | LINKED | LINKED | LINKED | NO |
| Vital signs | LINKED | LINKED | LINKED | NO |
| Lab results | LINKED | LINKED | LINKED | NO |
| Messages | LINKED | LINKED | LINKED | NO |
| Team assignments | LINKED | LINKED | If Active | NO |
| Alert notifications | LINKED | LINKED | If Active | NO |
| Information sharing requests | LINKED | LINKED | If Active | NO |
| Case- and Entity-Specific Elements | | | | |
| Case start time | NO | NO | NO | YES |
| Case stop time | NO | NO | NO | YES |
| Patient arrival time | NO | NO | NO | YES |
| Case-specific treatment activities | NO | NO | NO | NO |
| Case-specific evaluation scores | NO | NO | NO | NO |
| QA data elements | NO | NO | Local only | Local only |
| Transfer Data | | | | |
| Transfer departure time | NO | NO | NO | YES |
| Transfer arrival time | NO | NO | NO | YES |
| Transferring facility | NO | NO | NO | YES |
| Receiving facility | NO | NO | NO | YES |
| Transporting agency | NO | NO | NO | YES |
| Consult entity and time | NO | NO | NO | YES |

Table 1 includes, for each data element within one of several categories of data elements, an indication of whether or not the data element represents shared data that is automatically synchronized across healthcare entities, linked data that is visible by, but not synchronized with, other healthcare entities, or entity-owned data that is neither synchronized between healthcare entities nor visible to users at a healthcare entity other than a healthcare entity that owns the entity-specific information. For example, only those data elements for which the value in the Copy on Request column is YES may be included in a new entity-specific copy of an aggregate healthcare record created in response to an information sharing request. Similarly, only those data elements for which the value in the Synchronize on Client Devices column is YES may be synchronized across healthcare entities on the dedicated patient communication channel in response to an addition or modification of the data element at one of the healthcare entities. In another example, those data elements for which the value in the Copy on Request column and/or the Synchronize on Client Devices column is LINKED may be visible to, but not synchronized across, all the healthcare entities on the dedicated patient communication channel. In some embodiments and under certain circumstances, when a linked data element is added or modified, the inter-facility communication platform may sent a push notification to all of the healthcare entities on the dedicated patient communication channel indicating that the data element has been added or modified.

Most, if not all, of the data elements in a same category may be subject to the same or similar medical information sharing rules. For example, all of the data elements in the Patient Demographic Data category are shared data elements that are automatically synchronized across healthcare entities in real time. In another example, all of the data elements in the Additional Patient Related Data category are linked data elements that are visible by, but not synchronized across, all healthcare entities that are active on the dedicate patient communication channel. Some of the data elements that are not designated for automatic sharing or linking may represent data elements that are designated as private information that is only visible at the healthcare entity that owns the information. For example, data representing quality improvement (QI) or quality assurance (QA) information may only be visible locally at the source healthcare entity.

As previously noted, a handoff type request is intended to facilitate a process in which a patient is actually handed off to another facility, whereas a consult type request is used only for communication between healthcare entities. In some embodiments, there may be medical information sharing rules in which particular data elements are treated differently depending on whether the information sharing request is a consult type request or a handoff type request. For example, in some embodiments, a transfer request must be either accepted or declined by the receiving facility, and there are UI affordances to support the accept/decline workflow. In some embodiments, there are team configuration options that allow for automatic assignment of additional teams at the receiving facility when a transfer request is accepted. In one example, teams A and B may be assigned and alerted when a transfer is requested, while teams B, C, and D may be assigned and alerted when the transfer is accepted. In this example, teams B, C, and D would not ever be alerted if the transfer is declined.

In some embodiments, there are automatic rules about communication that apply in the case of handoff type requests, but not in the case of consult type requests. For example, in some embodiments, every team member at both an originating entity and a receiving entity receives a push alert when a transfer is requested and every team member at both the originating entity and the receiving entity receives a push alert when a transfer is accepted, which is not the case for consult type requests. In another example, once the door time is set for the facility receiving the transfer, the communication platform may stop sending patient communication channel updates and other messages to the originating facility. In some embodiments, an exception to this approach may be that a stopped case message may be sent to all team members to notify them about the conclusion of the patient's treatment. Similarly, in some embodiments, the communication platform may stop sending patient communication channel updates and other messages to an EMS agency that transports the patient to a receiving facility once the door time is set at the receiving facility, even if there is not a transfer request in play.

FIGS. 3A through 3D, 4A through 4F, and 5A through 5H illustrate example scenarios in which the systems and method described herein may be used to exchange medical information between healthcare entities over dedicated patient communication channels using consult type information sharing requests and transfer type information sharing requests.

FIGS. 3A through 3D illustrate an example scenario in which medical information associated with a given patient is exchanged between two hospitals and an Emergency Medical Services (EMS) agency, according to some embodiments. More specifically, FIGS. 3A through 3D illustrate an example scenario in which a first hospital, shown as hospital 1 (310) consults with a second hospital, shown as hospital 2 (330) regarding a given patient, after which hospital 1 (310) issues a handoff type request to transfer the given patient to hospital 2 (330). The transfer includes an additional handoff request to a transporting agency, shown as EMS agency 1 (320) to transport the given patient from hospital 1 (310) to hospital 2 (330).

Figure 3A:
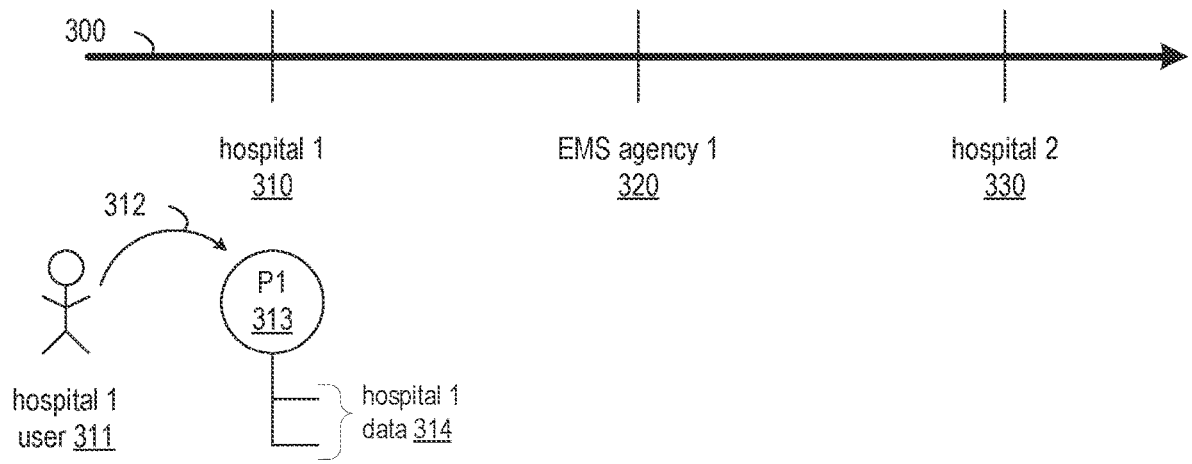
FIGS. 3A-3D, 4A-4F, 5A-5H illustrate respective example scenarios in which data associated with a particular individual is exchanged, according to some embodiments.

As illustrated in FIG. 3A, in this example, a hospital 1 user (311) may initiate the creation of a dedicated communication channel, represented in FIG. 3A as channel 300, for the given patient and an aggregate healthcare record, an entity-specific copy of which is shown as P1 (313), for the given patient. The hospital 1 user (311) may be a healthcare provider, such as a doctor, a nurse, or another user that provides healthcare services to patients, or an administrator at hospital 1 (310) operating a client computing device configured to exchange medical information with other users operating client computing devices at hospital 1 and at other healthcare entities with which hospital 1 has an inter-entity relationship through communications managed by an inter-facility communication platform (not shown in FIG. 3A). For example, in various embodiments, only users assigned to provide healthcare services to the given patient as part of a patient-specific care team or other users authorized to exchange medical information associated with the given patient.

In at least some embodiments, initiating the creation of the dedicated communication channel 300 and the aggregate healthcare record, as well as the entity-specific copy of the aggregate healthcare record shown as P1 (313), may include selecting, on a client computing device at hospital 1 (310), an operation to open a new case for the given patient at hospital 1 (310). This operation may take the form of a create channel request (312) that is detected or received by the inter-facility communication platform. The inter-facility communication platform may, in various embodiments, establish the dedicated communication channel 300 for the given patient using any of the communication technologies and protocols described herein or another suitable communication technology or protocol.

The inter-facility communication platform may also create the aggregate healthcare record and the entity-specific copy of the aggregate healthcare record shown as P1 (313), which may be stored locally on the inter-facility communication platform or in cloud-based storage, for example, in different embodiments. Once the aggregate healthcare record and the entity-specific copy of the aggregate healthcare record shown as P1 (313) are created, users at hospital 1 (310) may add data to the entity-specific copy of the aggregate healthcare record P1 (313). This may include, for example, demographic data for the given patient as well as case-specific and/or entity-specific data. As described herein, in at least some embodiments, patient demographic data may be shared and synchronized between multiple entity-specific copies of the aggregate healthcare record, including P1 (313), as information is added and modified by authorized users at healthcare entities involved in the given patient's care. At least some of the case-specific and/or entity-specific data added by hospital 1 users, such as hospital 1 user (311), may be linked data that is visible across healthcare entities, but is not synchronized across healthcare entities. This information, which is shown in FIG. 3A as hospital 1 data (314), may include, for example, patient arrival time, lab results, or other entity-specific information.

Figure 3B:
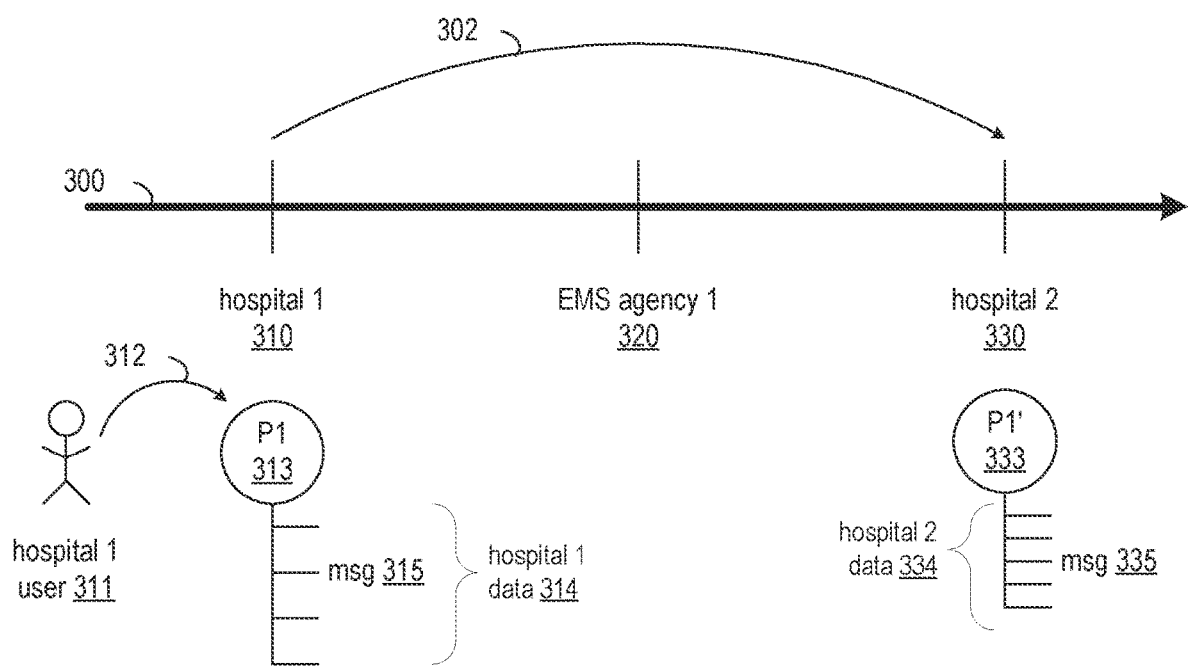

As illustrated in FIG. 3B, a user at hospital 1 (310), such as hospital user 1 (311), may initiate an information sharing request that is associated with the given patient and directed to hospital 2 (330) as the target recipient. For example, hospital 2 (330) may be a hub hospital, such as a regional hospital with expertise in certain disciplines that is not available at hospital 1 (310). In this example, hospital user 1 (311) may send a message to hospital 2 (330) requesting an opinion about whether or not, in their expert opinion, the given patient should be transferred. This type of consult request may be common for stroke patients, for example. Initiating the information sharing request may include selecting, on a client computing device at hospital 1 (310), an operation to consult with a recipient team or individual at hospital 2 (330). This operation may take the form of a consult request (302) that is detected or received by the inter-facility communication platform. The inter-facility communication platform may add hospital 2 (330) to the dedicated communication channel 300 for the given patient in response to consult request 302.

In response to the consult request 302, the inter-facility communication platform creates an entity-specific copy, shown as P1' (333), of the aggregate healthcare record associated with the given patient for the receiving hospital using a copy-on-request operation (not shown). The entity-specific copy may be created by the inter-facility communication platform as defined by applicable medical information sharing rules. Once the entity-specific copy P1' (333) is created and the consult request 302 is accepted, a user at hospital 2 (330) may add entity-specific data, shown as hospital 2 data (354) to the entity-specific copy P1' (333).

In some embodiments, users at hospital 1 (310) and hospital 2 (330) may exchange messages regarding the condition of the given patient and recommendations for treatment at hospital 1 (310) or for transferring the given patient to hospital 2 (330). For example, a user at hospital 1 (310), such as hospital user 1 (311), may send one or more messages 315 to a recipient team or individual at hospital 2 (330) over dedicated communication channel 300, and a user at hospital 2 (230) may send one or more messages 335 to a recipient team or individual at hospital 1 (310) over dedicated communication channel 300. In at least some embodiment, messages 315 may be added to the entity-specific copy of the aggregate healthcare record for hospital 1 (310), shown as P1 (313), and messages 335 may be added to the entity-specific copy of the aggregate healthcare record for hospital 2 (330), shown as P1' (333). For example, a user at hospital 2 (230) may indicate, through one of the messages 335 that, based on their symptoms, the patient should be transported to hospital 2 (330), which is better equipped to treat the patient than hospital 1 (310).

Figure 3C:
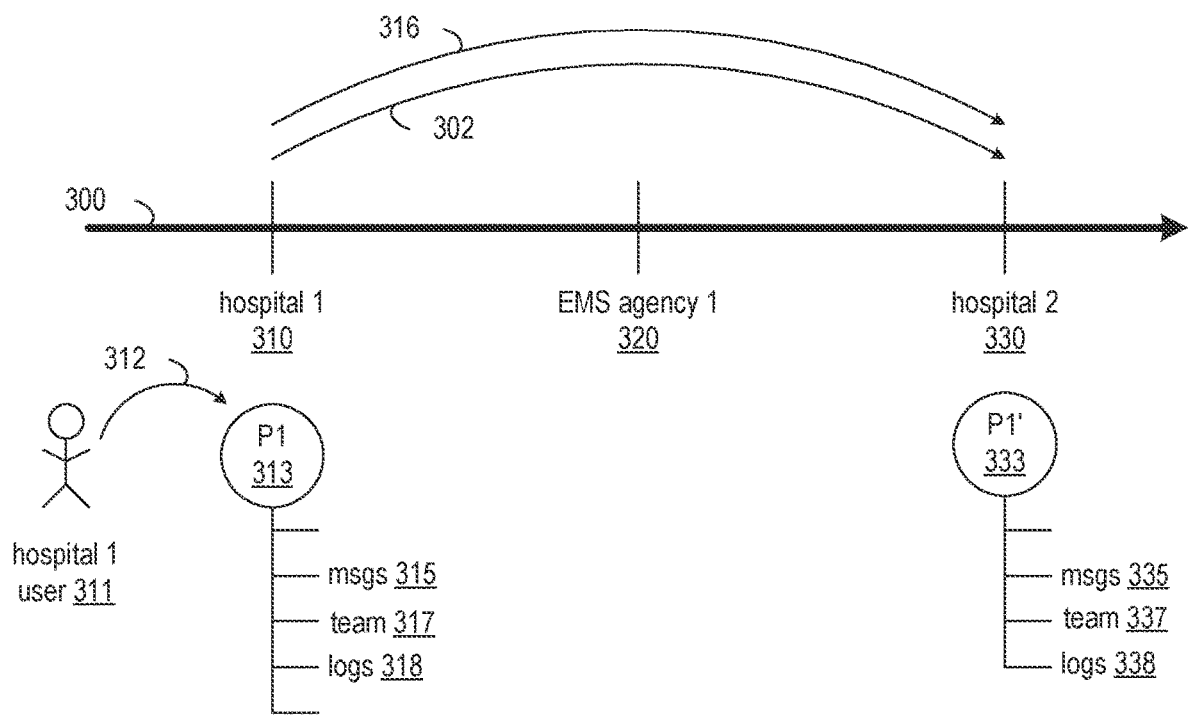

As illustrated in FIG. 3C, if, based on consultation with hospital 2 (330), a user at hospital 1 (310), such as hospital user 1 (311), determines that the given patient should be transferred to hospital 2 (330), the user at hospital 1 may initiate a handoff type request to transfer the given patient to hospital 2 (330) as the receiving facility. Initiating the handoff request may include selecting, on a client computing device at hospital 1 (310), an operation to transfer the given patient to hospital 2 (330). This operation may take the form of a transfer request (316) that is detected or received by the inter-facility communication platform. In this example, hospital 2 (330) has already been added to the dedicated communication channel 300 for the given patient. In this example, since an entity-specific copy of the aggregate healthcare record, shown as P1' (333), has already been created in response to consult request 302, there may be no need to create another entity-specific copy of the aggregate healthcare record for hospital 2 (330) in response to the handoff type request 316.

In at least some embodiments, data representing both the consult request 302 and the handoff type request 316 may be added to the entity-specific copies of the aggregate healthcare record for hospital 1 (310) and hospital 2 (330), shown as P1 (313) and P1' (333), respectively. As shown in FIG. 3C, the entity-specific copy P1 (313) of the aggregate healthcare record for hospital 1 (310) may, at this point, include messages 315, team information 317 indicating which users at hospital 1 (310) have been assigned to the given patient and their roles, and entity- or case-specific logs 318. Similarly, the entity-specific copy P1' (333) of the aggregate healthcare record for hospital 1 (310) and hospital 2 (330) may, at this point, include messages 335, team information 337 indicating which users at hospital 2 (330) have been assigned to the given patient and their roles, and entity- or case-specific logs 338. In some embodiments, logs 318 and 338 may include, for example, activity and/or treatment logs. In some embodiments, logs 318 and 338 may include data representing information sharing requests sent or received over the dedicated communication channel 300.

Figure 3D:
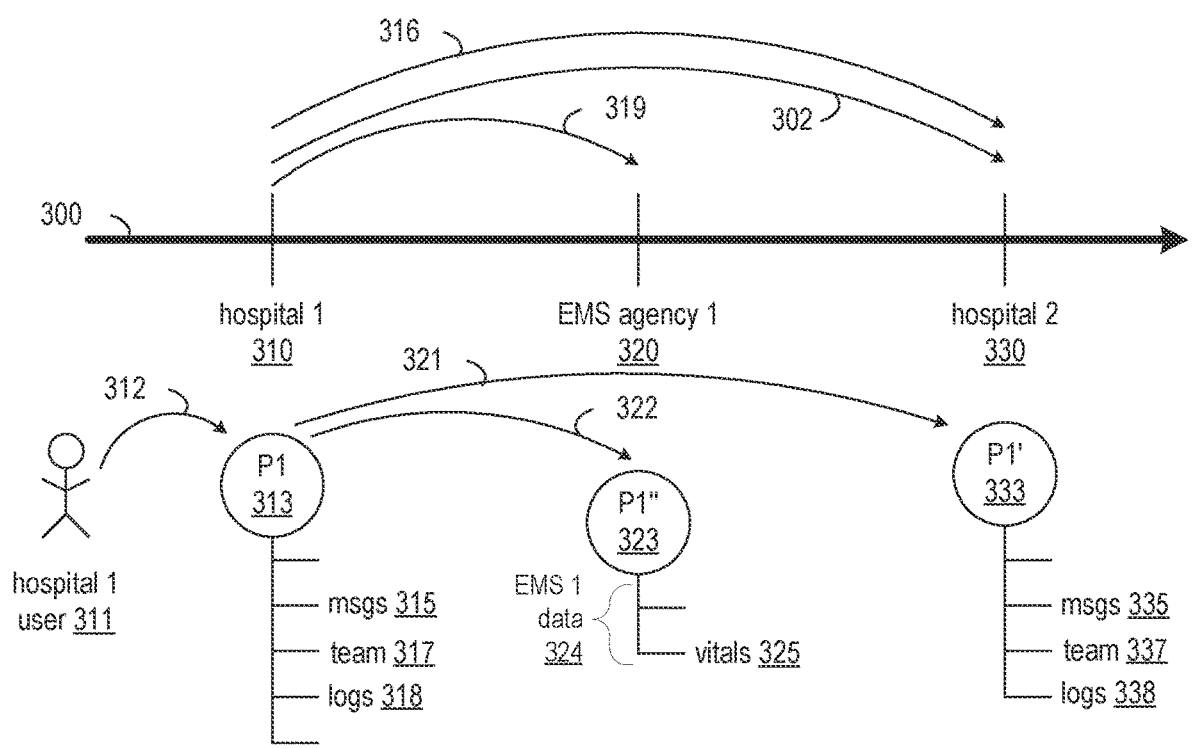

As illustrated in FIG. 3D, once hospital 2 (330) has accepted the handoff request (not shown), a user at hospital 1 (310), such as hospital user 1 (311), may initiate another handoff type request directed a transporting agency, such as EMS agency 1 (320) to transport the given patient from hospital 1 (310) to hospital 2 (330). In some embodiments, initiating the handoff request may include selecting, on a client computing device at hospital 1 (310), an operation to transport the given patient from hospital 1 (310) to hospital 2 (330). This operation may take the form of a transport request (319) that is detected or received by the inter-facility communication platform. In this example, EMS agency 1 (320) may be added to the dedicated communication channel 300 for the given patient. In addition, an entity-specific copy of the aggregate healthcare record, shown as P1'' (323), may be created in response to transport request 319 using a copy-on-request operation, shown as 322. Once the entity-specific copy P1'' (323) is created and EMS agency 1 (320) accepts the transport request 319, a user at EMS agency 1 (320) may add entity-specific data, shown as EMS 1 data (324) to the entity-specific copy P1'' (323). For example, a user at EMS agency 1 (320) may add vital signs, while the patient and the EMS user are in transit, and the communication platform may send a push notification to all healthcare entities on the dedicated patient communication channel indicating that vital signs have been added or modified.

In some embodiments, once a given patient has been transported to a receiving facility in response to a transfer request and/or a transport request, the entity initiating the transfer and any transporting agency involved in transporting the given patient from the initiating entity to the receiving facility may be removed from the dedicated communication channel for the given patient.

FIGS. 4A through 4F illustrate an example scenario in which medical information associated with a given patient is exchanged between an EMS agency, a medical control agency, and a hospital, according to some embodiments.

More specifically, FIGS. 4A through 4F illustrate an example of a healthcare service model in which a third-party medical control agency acts as a gatekeeper between other healthcare entities. In the illustrated example, a user shown as EMS 1 medic 405 at an EMS agency 1 (410) may consult with a third-party party medical control agency 1 (420) regarding a given patient and, if approved by the third-party medical control agency 1 (420), may then initiate a transfer of the given patient to a hospital 1 (430).

Figure 4A:
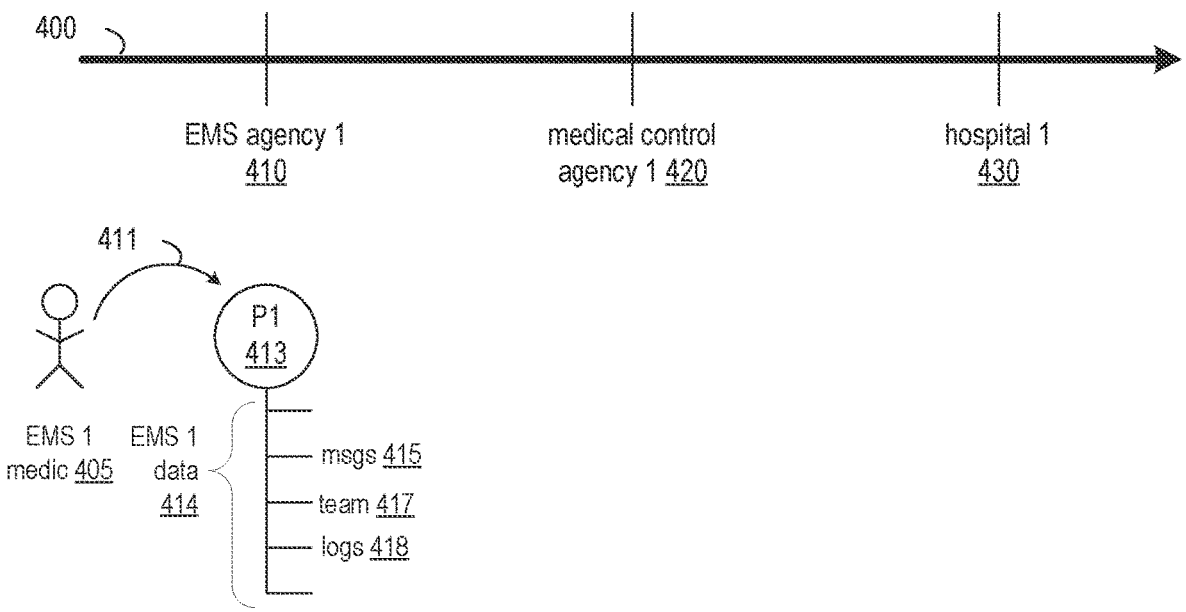

As illustrated in FIG. 4A, in this example, EMS 1 medic 405 may initiate the creation of a dedicated communication channel, represented in FIG. 4A as channel 400, for the given patient and an aggregate healthcare record P1 (413) for the given patient. The EMS 1 medic 405 may operate a client computing device configured to exchange medical information with other users operating client computing devices at other healthcare entities with which EMS agency 1 (410) has an inter-entity relationship through communications managed by an inter-facility communication platform (not shown in FIG. 4A).

In at least some embodiments, initiating the creation of the dedicated communication channel 400 and the aggregate healthcare record, as well as the entity-specific copy of the aggregate healthcare record shown as P1 (413), may include selecting, on a client computing device at EMS agency 1 (410), an operation to open a new case for the given patient at EMS agency 1 (410). This operation may take the form of a create channel request (411) that is detected or received by the inter-facility communication platform. The inter-facility communication platform may establish the dedicated communication channel 400 for the given patient using any of the communication technologies and protocols described herein or another suitable communication technology or protocol.

The inter-facility communication platform may also create the aggregate healthcare record and the entity-specific copy of the aggregate healthcare record shown as P1 (413), which may be stored locally on the inter-facility communication platform or in cloud-based storage, for example, in different embodiments. Once the aggregate healthcare record and the entity-specific copy of the aggregate healthcare record shown as P1 (413) are created, users at EMS agency 1 (410), such as EMS 1 medic 405, may add data to the entity-specific copy of the aggregate healthcare record P1 (413). This may include, for example, demographic data for the given patient as well as case-specific and/or entity-specific data. As described herein, in at least some embodiments, patient demographic data may be shared and synchronized between multiple entity-specific copies of the aggregate healthcare record, including P1 (413), as information is added and modified by authorized users at healthcare entities involved in the given patient's care. At least some of the case-specific and/or entity-specific data added by EMS agency 1 users, such as EMS 1 medic 405, may be linked data that is visible across healthcare entities, but is not synchronized across healthcare entities. This information, which is shown in FIG. 4A as EMS 1 data (414), may include, for example, messages 415, team information 417 indicating which users at EMS agency 1 (410) have been assigned to the given patient and their roles, and entity- or case-specific logs 418. In some embodiments, logs 418 may include, for example, activity and/or treatment logs. In some embodiments, logs 418 may include data representing information sharing requests sent or received over the dedicated communication channel 400.

Figure 4B:
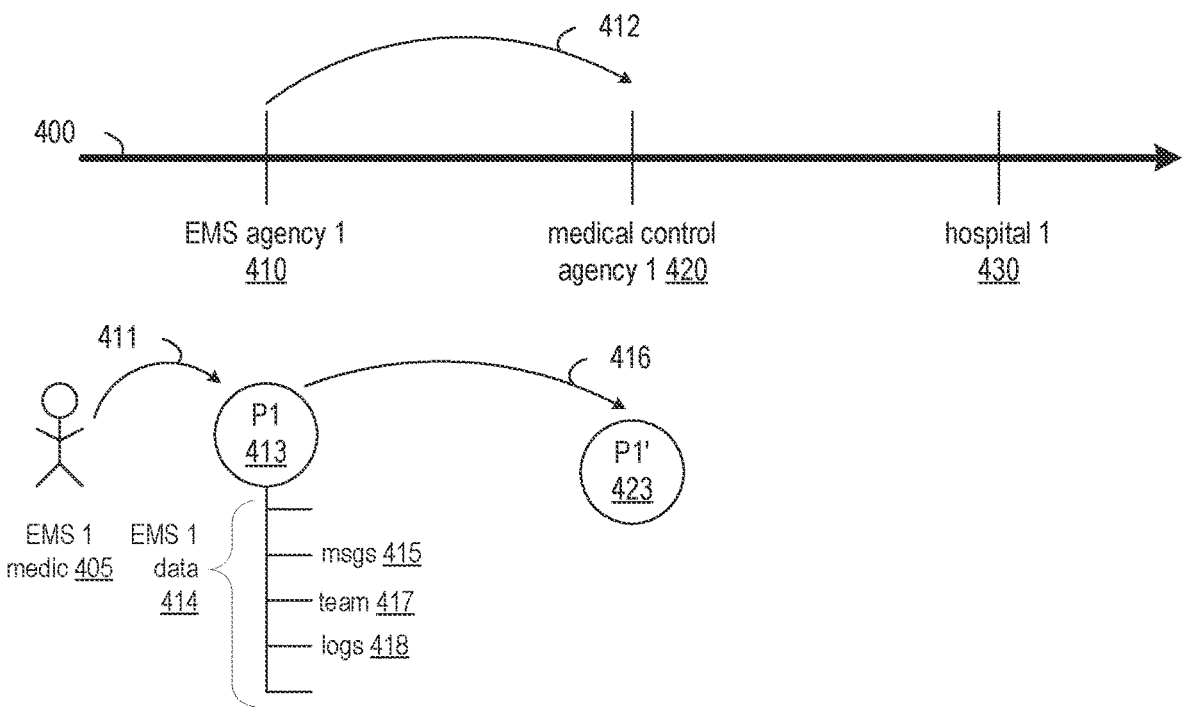

As illustrated in FIG. 4B, a user at EMS agency 1 (410), such as EMS 1 medic 405, may initiate an information sharing request that is associated with the given patient and directed to medical control agency 1 (420) as the target recipient. For example, medical control agency 1 (420) may serve as a gatekeeper for certain interactions between healthcare facilities that have inter-entity relationships, such as EMS agency 1 (410) and hospital 1 (430). Initiating the information sharing request may include selecting, on a client computing device at EMS agency 1 (410), an operation to consult with a recipient team or individual at medical control agency 1 (420). This operation may take the form of a consult request (412) that is detected or received by the inter-facility communication platform. The inter-facility communication platform may add medical control agency 1 (420) to the dedicated communication channel 400 for the given patient in response to consult request 412.

In response to consult request 412, the inter-facility communication platform creates an entity-specific copy, shown as P1' (423), of the aggregate healthcare record associated with the given patient for the medical control agency 1 (420) using a copy-on-request operation (416). The entity-specific copy may be created by the inter-facility communication platform as defined by applicable medical information sharing rules. In at least some embodiments, data representing the consult request 412 may be added to the entity-specific copies of the aggregate healthcare record for EMS agency 1 (410) and medical control agency 1 (420), shown as P1 (413) and P1' (423), respectively.

Figure 4C:
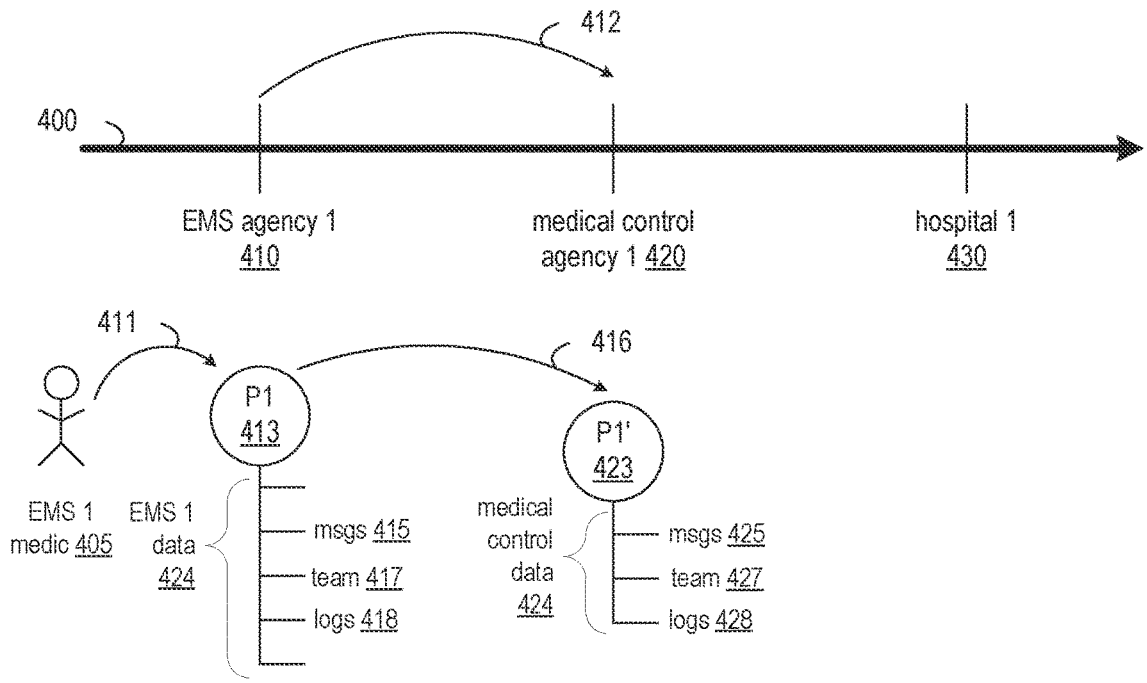

As shown in FIG. 4C, once the entity-specific copy P1' (423) is created and the consult request 412 is accepted, a user at medical control agency 1 (420) may add entity-specific data, shown as medical control data (424) to the entity-specific copy P1' (423). In some embodiments, users at EMS agency 1 (410) and hospital 1 (430) may exchange messages regarding the condition of the given patient and recommendations for treatment by EMS agency 1 (410) or for transferring the given patient to hospital 1 (430). For example, a user at EMS agency 1 (410), such as EMS 1 medic 405, may send one or more messages 415 to a recipient team or individual at medical control agency 1 (420) over dedicated communication channel 400, and a user at medical control agency 1 (420) may send one or more messages 425 to a recipient team or individual at EMS agency 1 (410) over dedicated communication channel 400. In at least some embodiment, messages 415 may be added to the entity-specific copy of the aggregate healthcare record for EMS agency 1 (410), shown as P1 (413), and messages 425 may be added to the entity-specific copy of the aggregate healthcare record for medical control agency 1 (420), shown as P1' (423). In one example, a user at medical control agency 1 (420) may send a message 425 to a recipient team or individual at EMS agency 1 (410) recommending or authorizing the transfer of the patient to hospital 1 (430). In another example, a user at medical control agency 1 (420) may send a message 425 to a recipient team or individual at EMS agency 1 (410) recommending against, or declining to authorize, the transfer of the patient to hospital 1 (430). As shown in FIG. 4C, the entity-specific copy P1 (413) of the aggregate healthcare record for EMS agency 1 (410) may, at this point, include messages 415, team information 417 indicating which users at EMS agency 1 (410) have been assigned to the given patient and their roles, and entity- or case-specific logs 418. Similarly, the entity-specific copy P1' (423) of the aggregate healthcare record for medical control agency 1 (420) may, at this point, include messages 425, team information 427 indicating which users at medical control agency 1 (420) have been assigned to the given patient and their roles, and entity- or case-specific logs 428. In some embodiments, logs 418 and 428 may include, for example, data representing information sharing requests sent or received over the dedicated communication channel 400.

Figure 4D:
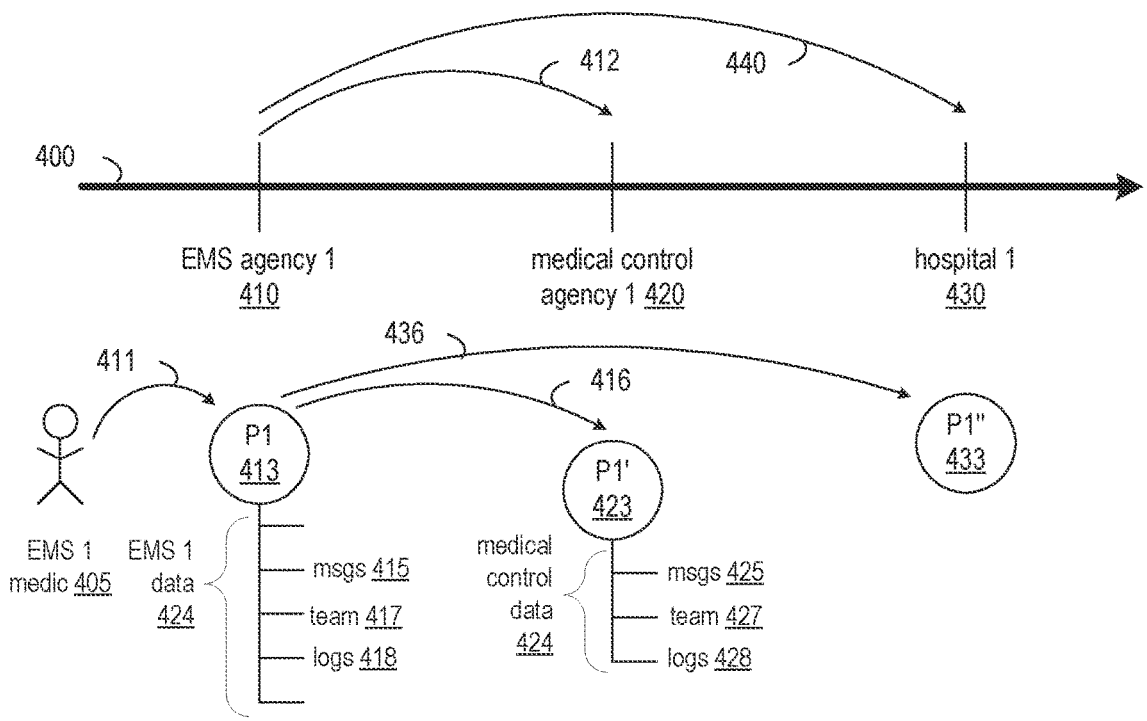
Figure 4E:
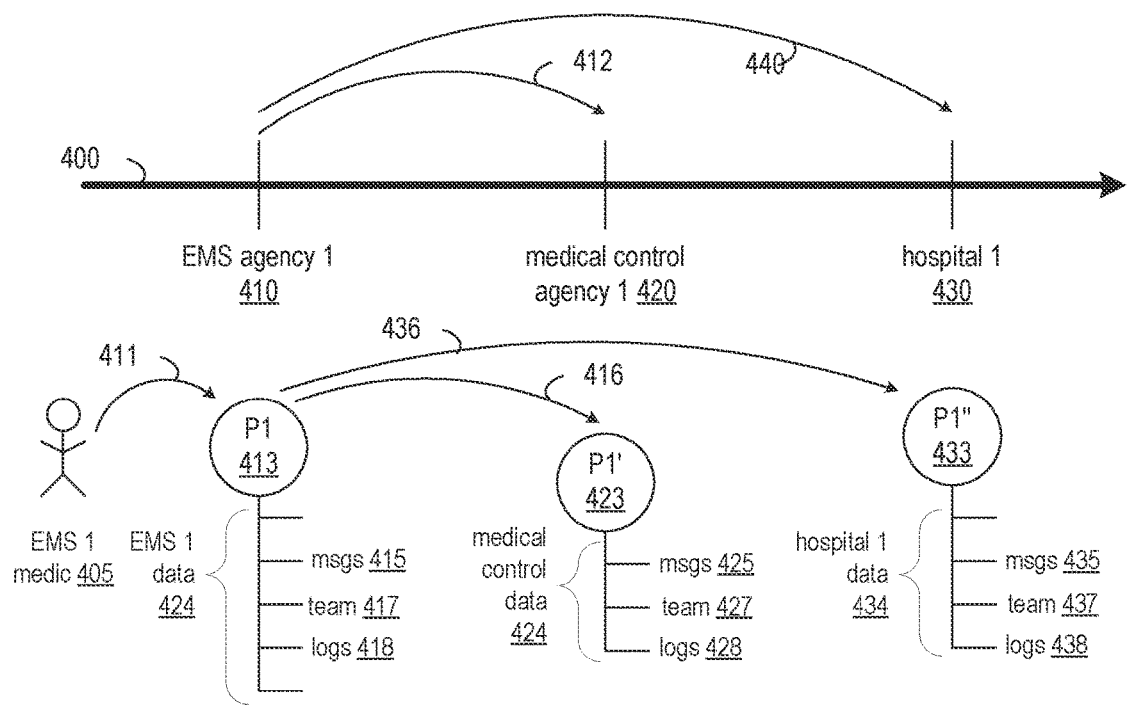

As illustrated in FIG. 4D, if, based on consultation with medical control agency 1 (420), a user at EMS agency 1 (410), such as EMS medic 1 405, determines that the given patient should be transferred to hospital 1 (430), the user at EMS agency 1 (410) may initiate a handoff type request to transfer the given patient to hospital 1 (430) as the receiving facility. Initiating the handoff request may include selecting, on a client computing device at EMS agency 1 (410), an operation to transfer the given patient to hospital 1 (430). This operation may take the form of a transfer request (440) that is detected or received by the inter-facility communication platform. In response to the transfer request 440, hospital 1 (430) may be added to the dedicated communication channel 400 for the given patient. In addition, an entity-specific copy of the aggregate healthcare record, shown as P1" (433), may be created for hospital 1 (430) in response to the handoff type request 440 using a copy-on-request operation shown as 436. In at least some embodiments, data representing handoff type request 440 may be added to the entity-specific copies of the aggregate healthcare record for EMS agency 1 (410) and hospital 1 (430), shown as P1 (413) and P1" (433), respectively.

As illustrated in FIG. 4D, once the entity-specific copy P1" (433) is created and the handoff request 440 is accepted, a user at hospital 1 (430) may add entity-specific data, shown as hospital 1 data (434), to the entity-specific copy P1" (433). In some embodiments, a user at EMS agency 1 (410), such as EMS 1 medic 405, may add or update patient information in the entity-specific copy of the aggregate healthcare record for EMS agency 1 (410), shown as P1 (413), while the given patient is being transported to hospital 1 (430). For example, EMS 1 medic 405 may add or update vital signs, while the patient and the EMS 1 medic 405 are in transit, and the communication platform may send a push notification to all healthcare entities on the dedicated patient communication channel indicating that vital signs have been added or modified. In some embodiments, users at EMS agency 1 (410) and hospital 1 (430) may exchange messages regarding the condition of the given patient prior to the arrival of the given patient at hospital 1 (430). For example, a user at EMS agency 1 (410), such as EMS 1 medic 405, may send one or more messages 415 to a recipient team or individual at hospital 1 (430) over dedicated communication channel 400, and a user at hospital 1 (430) may send one or more messages 435 to a recipient team or individual at EMS agency 1 (410) over dedicated communication channel 400. In at least some embodiment, messages 415 may be added to the entity-specific copy of the aggregate healthcare record for EMS agency 1 (410), shown as P1 (413), and messages 435 may be added to the entity-specific copy of the aggregate healthcare record for hospital 1 (430), shown as P1" (433). As shown in FIG. 4D, the entity-specific copy P1" (433) of the aggregate healthcare record for hospital 1 (430) may, at this point, include messages 435, team information 437 indicating which users at hospital 1 (430) have been assigned to the given patient and their roles, and entity- or case-specific logs 438. In some embodiments, logs 438 may include, for example, activity and/or treatment logs. In some embodiments, logs 438 may include data representing information sharing requests sent or received over the dedicated communication channel 400.

Figure 4F:
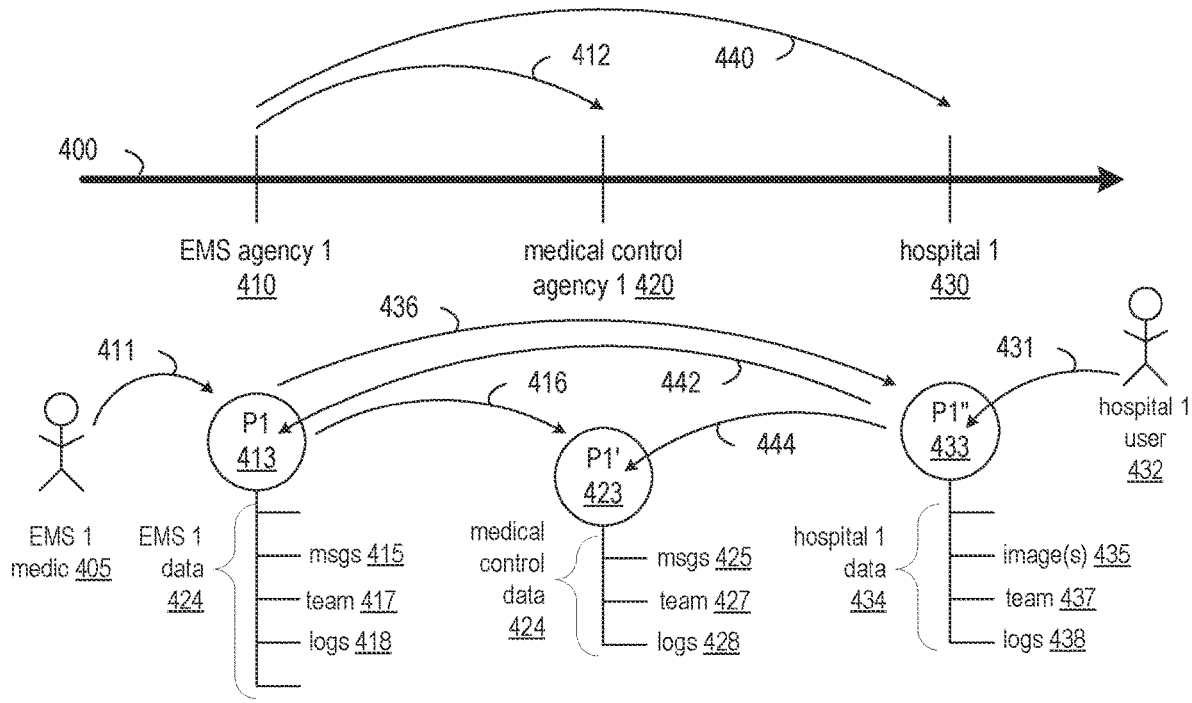

As illustrated in FIG. 4F, a user at hospital 1 (430), such as hospital 1 user (432), may add or modify patient information in the entity-specific copy of the aggregate healthcare record for hospital 1 (430), shown as P1" (433). This is shown as editing operation 431 in FIG. 4D. If the information added or modified includes shared patient data that is automatically synchronized across all healthcare entities that are active on the dedicated communication channel 400, it may be synchronized with the entity-specific copies of the aggregate healthcare record for EMS agency 1 (410) and medical control agency 1 (420), shown as P1 (413) and P1' (423), respectively. If the information added or modified does not include shared patient data that is automatically synchronized across healthcare entities, but is linked information, it may be visible to users at EMS agency 1 (410) and medical control agency 1 (420). In at least some embodiments, if linked information is added or modified by a user at one of the healthcare entities active on the dedicated communication channel 400, a notification indicating that the linked information has been added or changed may be pushed to client computing devices of users at the other healthcare entities active on the dedicated communication channel 400. In some embodiments, medical control agency may be removed from the dedicated communication channel 400 once a decision has been made about whether or not to transfer the patient or, if the decision is made to transfer the patient, once the patient has arrived at a receiving facility.

FIGS. 5A through 5H illustrate an example scenario in which medical information associated with a given patient is exchanged between a first responder, three EMS agencies, and two hospitals, according to some embodiments. This more complex example scenario includes multiple handoff type requests involving a given patient.

Figure 5A:
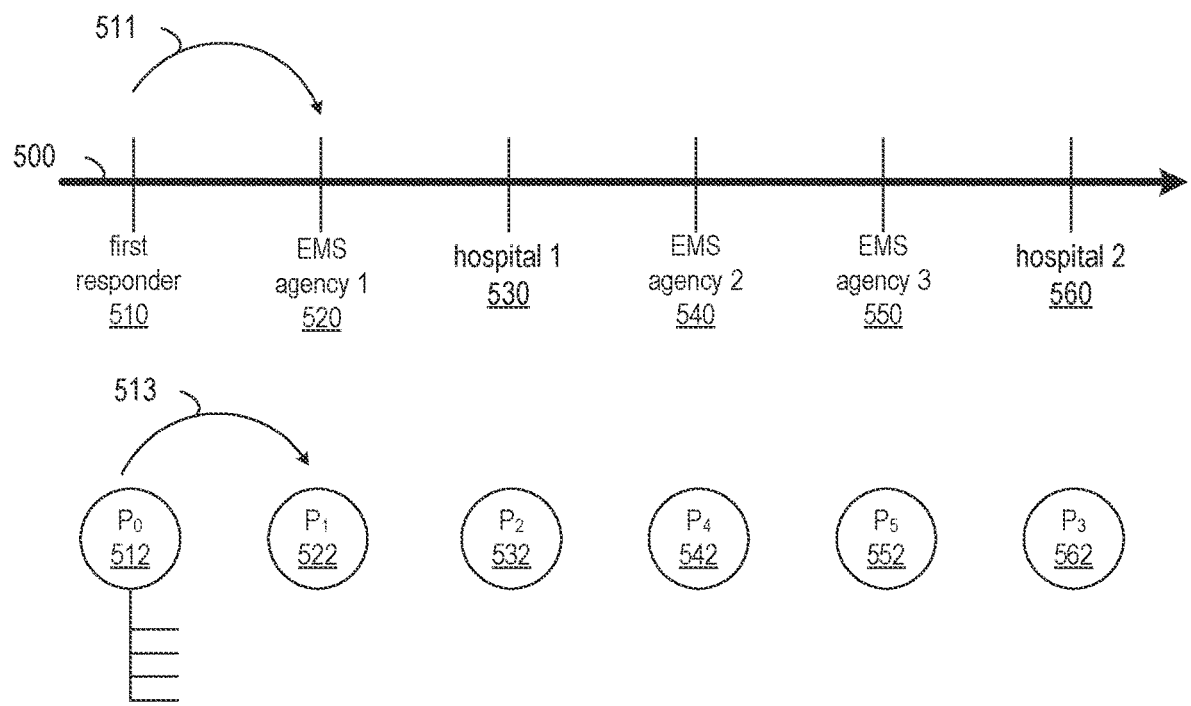

As illustrated in FIG. 5A, a first responder (510), such as a police officer or firefighter, may initiate a case for a given patient by requesting the creation, by an inter-facility communication platform, of a dedicated patient communication channel and a corresponding entity-specific copy of an aggregate healthcare record for the given patient, shown as $P_0$ (512). The first responder (510) may begin adding data to the entity-specific copy of an aggregate healthcare record $P_0$ (512). For example, the first responder (510) may obtain and enter patient demographic information, may take photographs of the patient, the scene, or a medicine list for the patient, may type in some messages to other first responders, and/or may record an audio clip about what they observe while examining the patient. The first responder (510) may then initiate a handoff request (511) to EMS agency 1 (520), in response to which EMS agency 1 (520) is added to the patient communication channel and an entity-specific copy of the aggregate healthcare record for the given patient, shown as $P_1$ (522), is created for EMS agency 1 (520) using a copy-on-request operation (513). The entity-specific copy, $P_1$ (522), may include the demographic information entered by the first responder (510) but not any messages, images, or audio clips entered by the first responder (510). However, some or all of this information may be visible to users at EMS agency 1 (520) as linked information once they are added to the patient communication channel.

Figure 5B:
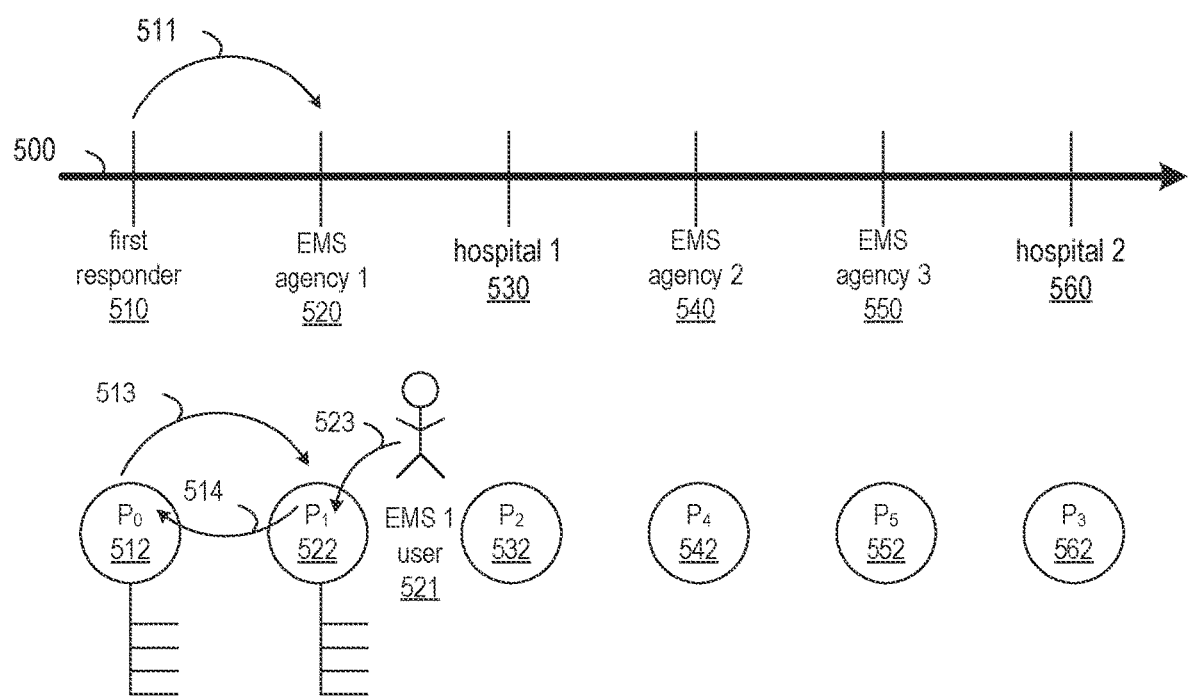

As illustrated in FIG. 5B, after accepting the handoff request 511, a user at EMS agency 1 (520), shown as EMS 1 user 521, may begin adding (at 523) data to the entity-specific copy, $P_1$ (522), and exchanging messages with the first responder (510). In one example, EMS 1 user 521 may add an image of the patient, or of an injury to the patient, once the patient has been collected for transport. If the information added to the entity-specific copy, $P_1$ (522), includes shared data, the communication platform may update (at 514) the shared data in $P_0$ (512) to synchronize it with the shared data in $P_1$ (522). For example, if the first responder (510) was not able to obtain the patient's birth date or entered an incorrect birth date for the patient, and EMS 1 user 521 was able to obtain and enter the correct birth date for the patient, this information may be updated in all other entity-specific copies of the aggregate healthcare record for the patient.

Figure 5C:
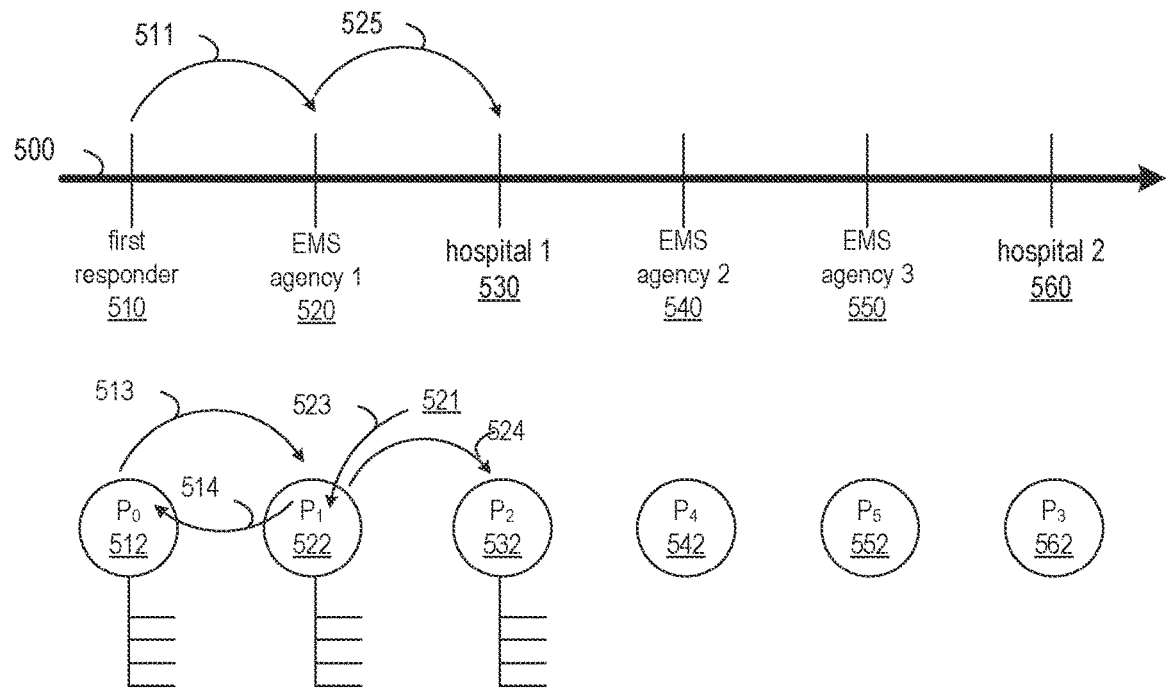

As illustrated in FIG. 5C, a user at EMS agency 1 (520), shown as EMS 1 user 521, may initiate a handoff request 525 to transport the patient to hospital 1 (530), in response to which hospital 1 (530) is added to the patient communication channel and an entity-specific copy of the aggregate healthcare record for the given patient, shown as $P_2$ (532), is created for hospital 1 (530) using a copy-on-request operation (524). The entity-specific copy, $P_2$ (532), may include the demographic information entered by the first responder (510) and/or the EMS 1 user (521), but not any messages, images, or audio clips entered by the first responder (510) or EMS 1 user (521). However, some or all of this information may be visible to users at hospital 1 (530) as linked information once they are added to the patient communication channel.

Figure 5D:
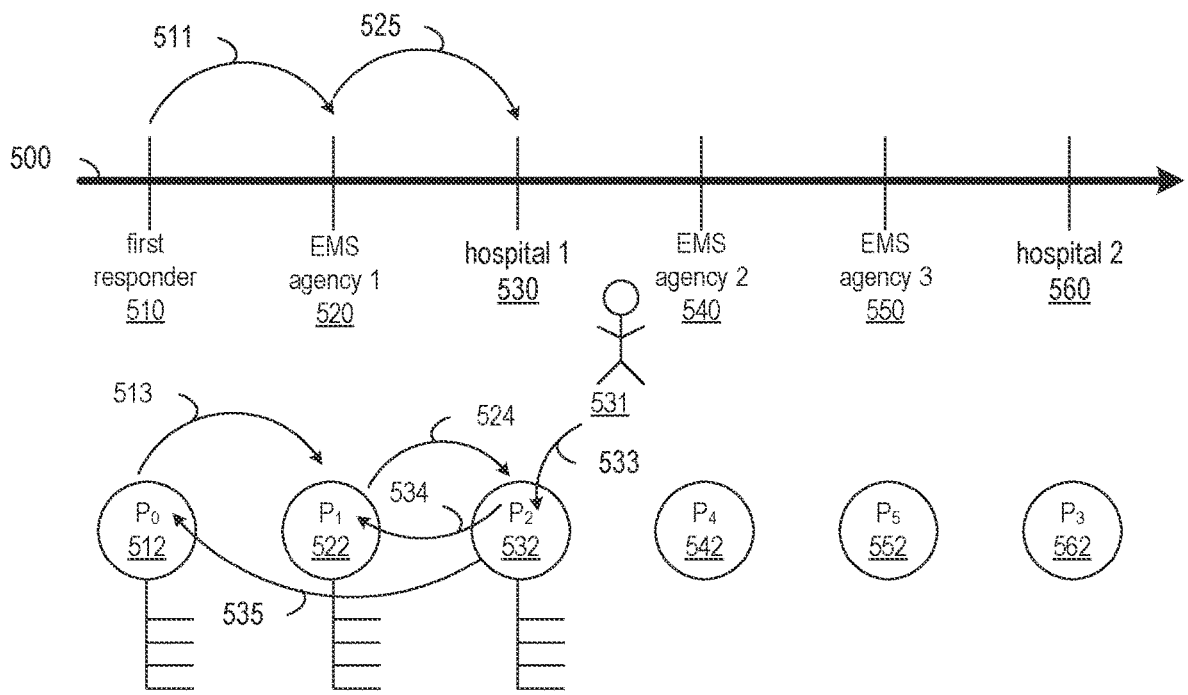

As illustrated in FIG. 5D, after accepting the handoff request 525, a user at hospital 1 (530), shown as user 531, may begin adding (at 533) data to the entity-specific copy, $P_2$ (532). For example, user 531 may add an image of an electrocardiogram (ECG) that was captured several months earlier as a baseline. If the information added to the entity-specific copy, $P_2$ (532), includes shared data, the communication platform may update (at 534) the shared data in $P_1$ (522) to synchronize it with the shared data in $P_2$ (532) and may update (at 535) the shared data in $P_0$ (512) to synchronize it with the shared data in $P_2$ (532).

Figure 5E:
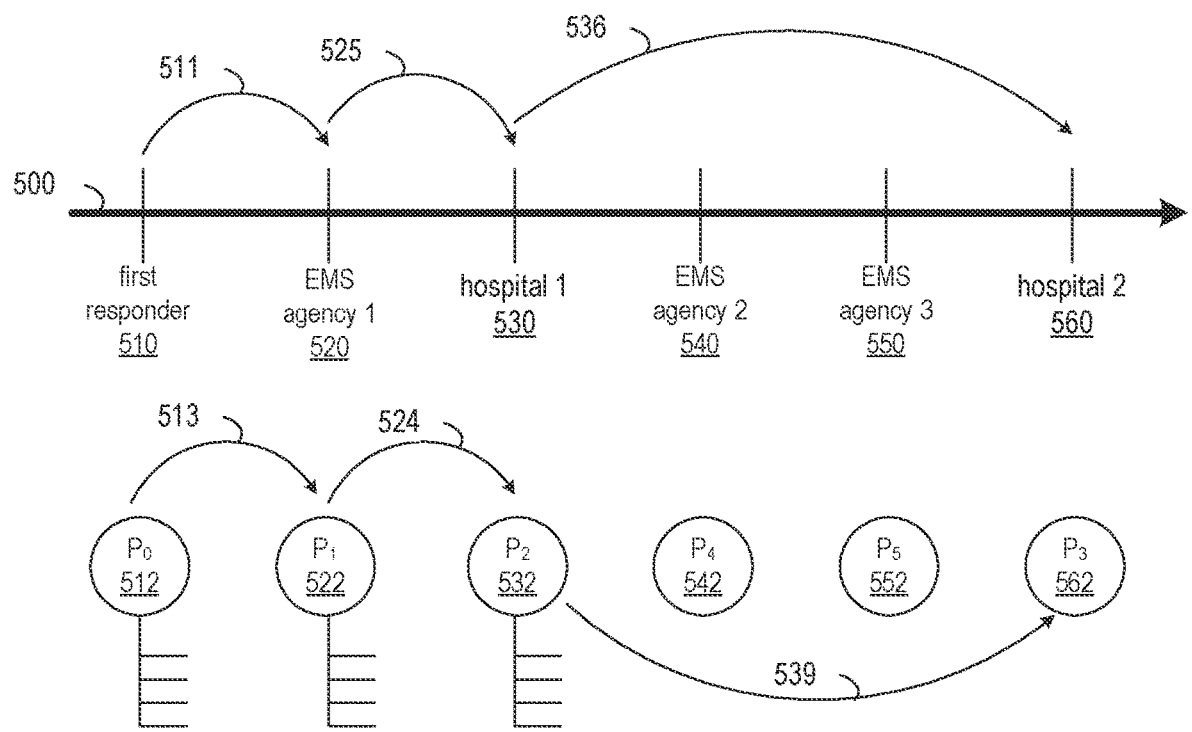

As illustrated in FIG. 5E, after one or more users at hospital 1 (530) have had a chance to triage the patient, one of the hospital 1 users may initiate a handoff request (536) to transfer the patient to a hospital that is better able to treat the patient. For example, if it is determined that the patient has suffered a heart attack or stroke, and hospital 2 (560) has a catheterization laboratory, the handoff request 536 may specify a request to transfer the patient to hospital 2 (560) to handle this time-critical situation. In response to handoff request 536, hospital 1 (530) is added to the patient communication channel and an entity-specific copy of the aggregate healthcare record for the given patient, shown as $P_3$ (562), is created for hospital 2 (560) using a copy-on-request operation (539). The entity-specific copy, $P_3$ (562), may include the demographic information entered by the first responder (510), the EMS 1 user (521), and/or a user at hospital 1 (530), but not any messages, images, or audio clips entered by these users. However, some or all of this information may be visible to users at hospital 2 (560) as linked information once they are added to the patient communication channel. Users at hospital 2 may, in some cases, add data to the entity-specific copy, $P_3$ (562), prior to the arrival of the patient (not shown).

Figure 5F:
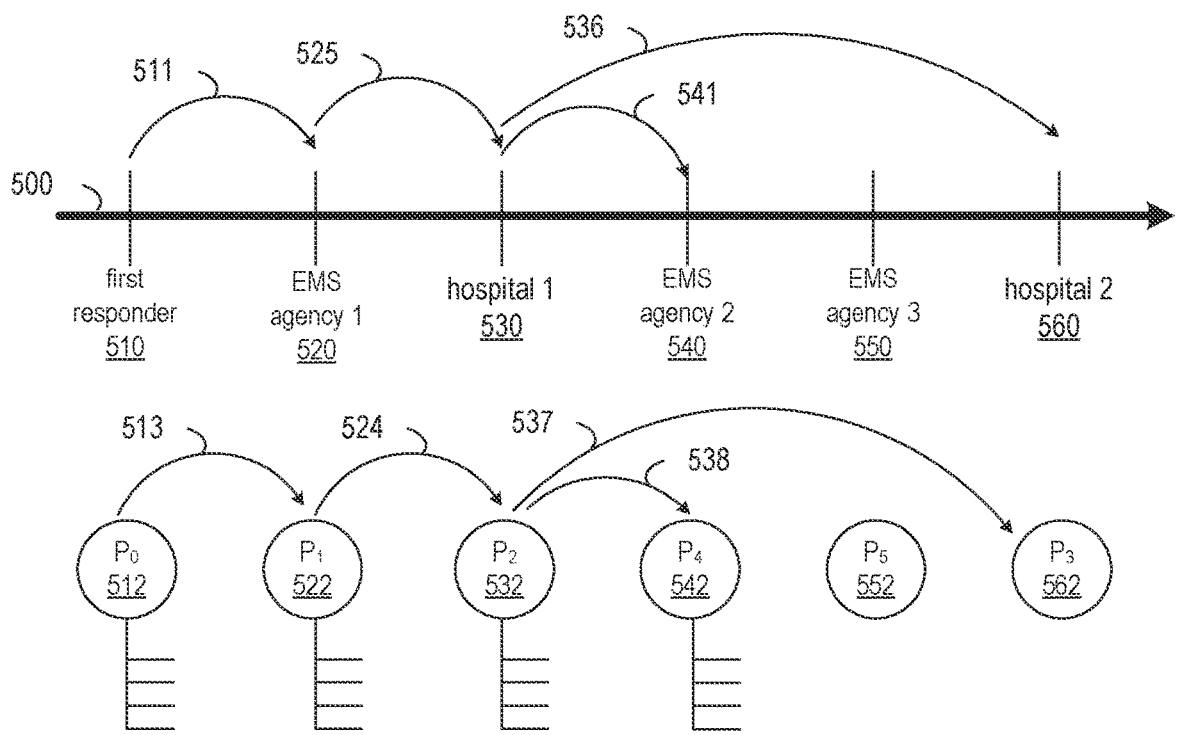

As illustrated in FIG. 5F, once hospital 2 (560) has accepted the handoff request 536, a user at hospital 1 (530) may initiate a handoff request (541) to EMS agency 2 (540) to transport the patient from hospital 1 (530) to hospital 2 (560). In response to handoff request 541, EMS agency 2 (540) is added to the patient communication channel and an entity-specific copy of the aggregate healthcare record for the given patient, shown as $P_4$ (542), is created for EMS agency 2 (540) using a copy-on-request operation (538). The entity-specific copy, $P_4$ (542), may include the demographic information entered by the first responder (510), the EMS 1 user (521), a user at hospital 1 (530), and/or a user at hospital 2 (560), but not any messages, images, or audio clips entered by these users. However, some or all of this information may be visible to users at EMS agency 2 (540) as linked information once they are added to the patient communication channel. Users at EMS agency 2 (540) may add information to the entity-specific copy, $P_4$ (542), such as vital sign data, image(s), or any other shared, linked, or entity-specific information (not shown).

Figure 5G:
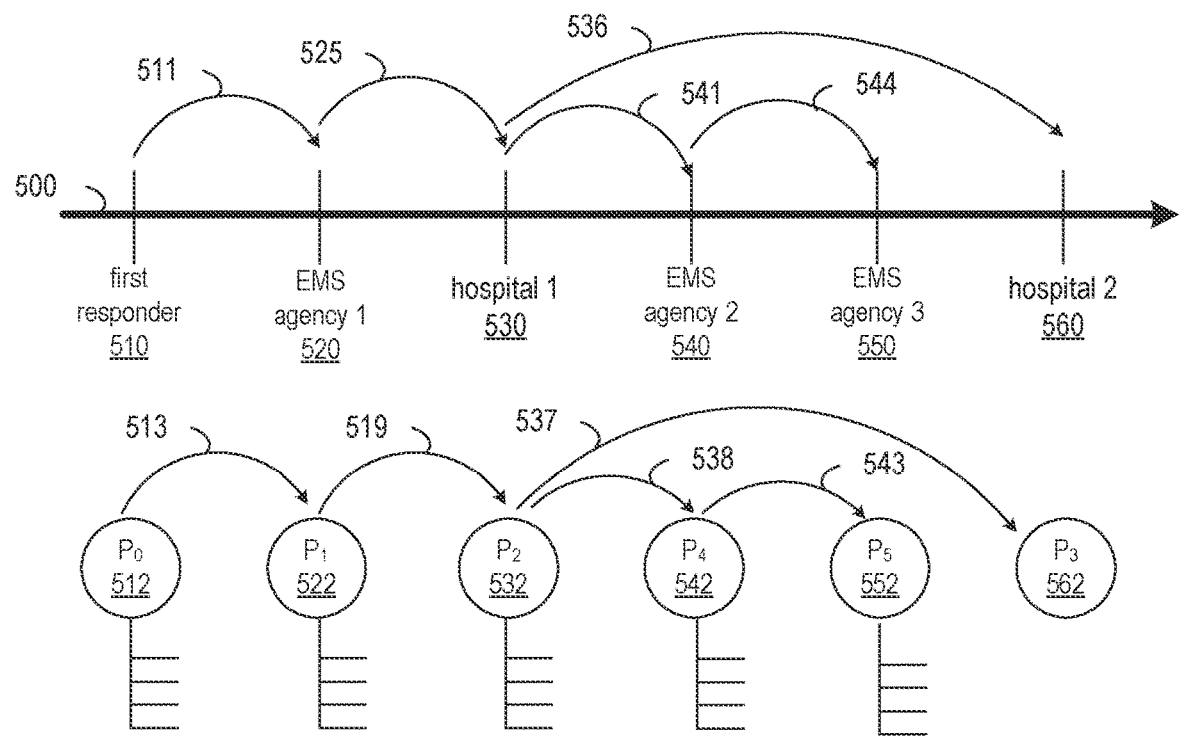

As illustrated in FIG. 5G, a user at EMS agency 2 (540) may determine that a faster method of transporting the patient, such as by helicopter, is warranted due to the time-critical nature of the case. In response, a user at EMS agency 2 (540) may initiate a handoff request 544 to EMS agency 3 (550) to transport the patient to hospital 2 (560). In response to handoff request 544, EMS agency 3 (550) is added to the patient communication channel and an entity-specific copy of the aggregate healthcare record for the given patient, shown as $P_5$ (552), is created for EMS agency 3 (550) using a copy-on-request operation (543). The entity-specific copy, $P_5$ (552), may include the demographic information entered by the first responder (510), the EMS 1 user (521), a user at hospital 1 (530), a user at hospital 2 (560), and/or a user at EMS agency 2 (540), but not any messages, images, or audio clips entered by these users. However, some or all of this information may be visible to users at EMS agency 3 (550) as linked information once they are added to the patient communication channel. Users at EMS agency 3 (550) may add information to the entity-specific copy, $P_5$ (552), such as an audio clip recorded while in flight. In some embodiments, business logic may be applied by the inter-facility communication platform to determine when and whether to push a notification to all healthcare entities active on the dedicated patient communication channel in response to the addition of certain data items. For example, such business logic may be applied to determine that a notification indicating that an audio clip has been added should be pushed to at least the team members at the destination, hospital 2 (560) so that they can receive the most up-to-date information about the patient prior to the patient's arrival.

Figure 5H:
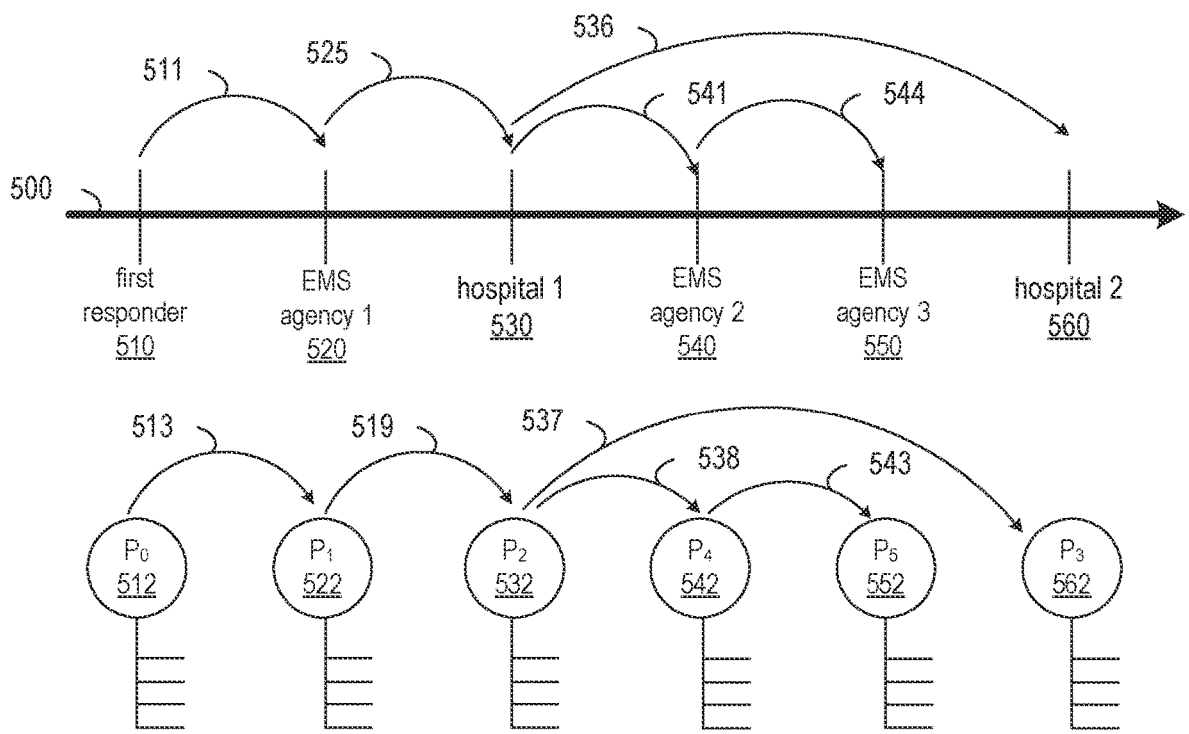

As illustrated in FIG. 5H, users at hospital 2 (560) may add data to the entity-specific copy, $P_3$ (562), following the arrival of the patient at hospital 2 (560). For example, a user at hospital 2 (560) may add vital sign data, image(s), or any other shared, linked, or entity-specific information (not shown). In addition, a user at hospital 2 (560) may add team information indicating which users at hospital 2 (560) have been assigned to the given patient and their roles, and entity- or case-specific logs. In some embodiments, the logs may include, for example, activity and/or treatment logs. In some embodiments, the logs may include data representing information sharing requests sent or received over a dedicated communication channel. In some embodiments, at this point, each entity-owned copy of the aggregate healthcare record for the given patient may include information identifying the assignment of particular users, e.g., healthcare providers, to the patient communication channel, activity and/or treatment logs, and logs of any sent or received consult or transfer requests, among other types of data.

Figure 6:
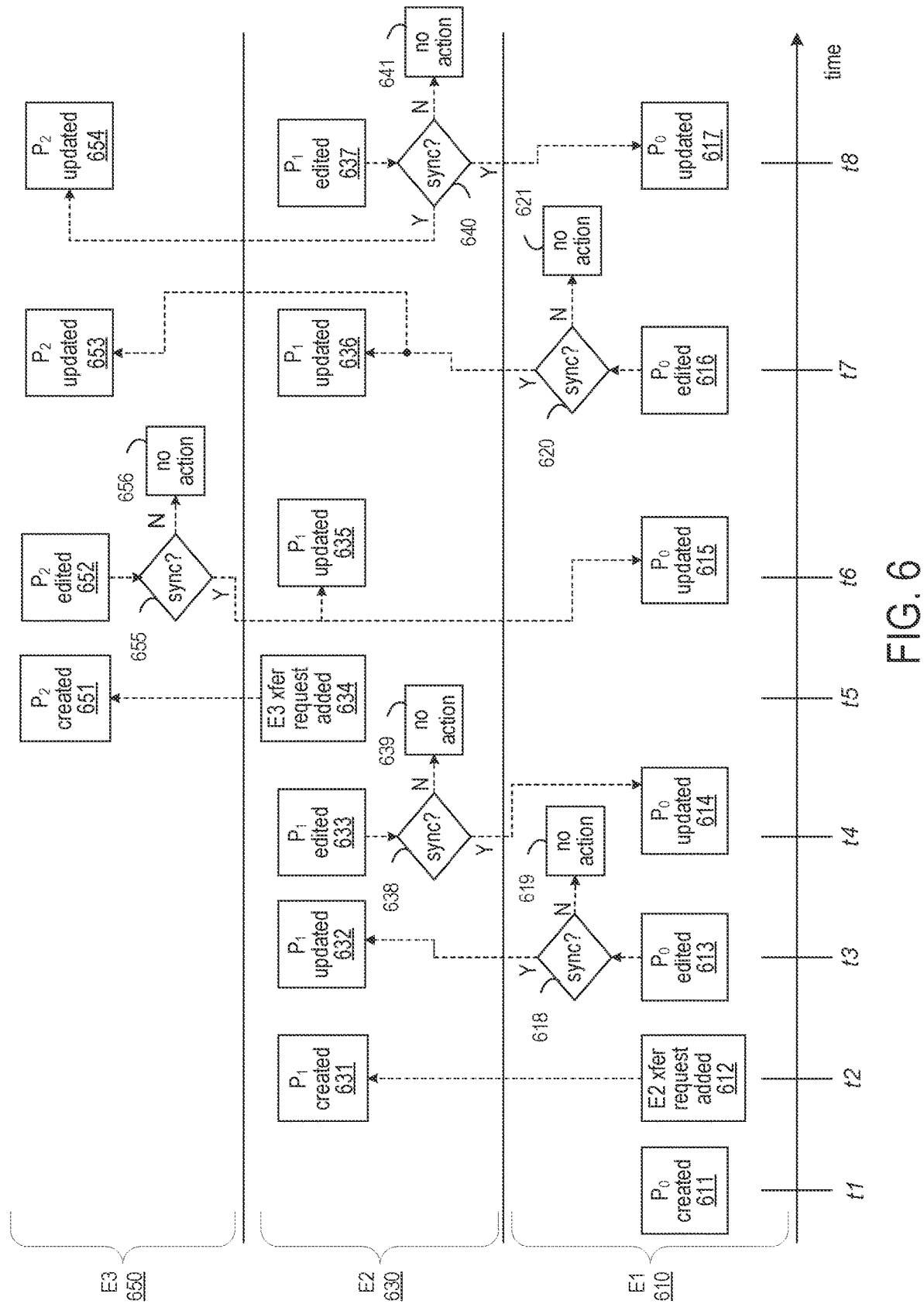
FIG. 6 illustrates an example scenario in which various copies of an aggregate record associated with a particular individual are edited and, in some cases synchronized, in accordance with some embodiments.

FIG. 6 illustrates an example scenario in which various copies of an aggregate healthcare record associated with a given patient are edited at particular healthcare entities and, in some cases, are synchronized to other healthcare entities, in accordance with some embodiments. Note that the relative times between events illustrated in FIG. 6 are merely illustrative and are not meant to imply any particular time scale on which certain events, or activities triggered by certain events, are performed.

In the illustrated example, three healthcare entities, shown as E1 610, E2 630, and E3 650 are, at different points in time, added to a dedicated communication channel for a given patient. As shown at 611 in FIG. 6, at time t1, an entity-specific copy $P_0$ of an aggregate healthcare record associated with the given patient is created for healthcare entity E1 610 and the dedicated communication channel for the given patient is created. One or more users at healthcare entity E1 610 may be added to the dedicated communication channel at this time.

As shown at 612, at time t2, a transfer request directed to healthcare entity E2 630 is added to the entity-specific copy $P_0$, triggering the creation of an entity-specific copy $P_1$ of the aggregate healthcare record for E2 630 through a copy-on-request operation. Subsequently, one or more users at healthcare entity E2 630 may be added to the dedicated communication channel.

As shown at 613, at time t3, a user at healthcare entity E1 610 edits entity-specific copy $P_0$, e.g., by adding or modifying information in the entity-specific copy $P_0$. If the edited information is shared information to be synchronized, shown as the positive exit from decision block 618, the editing may trigger an update to the shared information in the entity-specific copy $P_1$, shown at 632, to reflect the edits made at healthcare entity E1 610. However, if the edited information is not shared information to be synchronized, shown as the negative exit from decision block 618, no such action is taken, as in 619.

As shown at 633, at time t4, a user at healthcare entity E2 630 edits entity-specific copy $P_1$, e.g., by adding or modifying information in the entity-specific copy $P_1$. If the edited information is shared information to be synchronized, shown as the positive exit from decision block 638, the editing may trigger an update to the shared information in the entity-specific copy $P_0$, shown at 614, to reflect the edits made at healthcare entity E2 630. However, if the edited information is not shared information to be synchronized, shown as the negative exit from decision block 638, no such action is taken, as in 639.

As shown at 634, at time t5, a transfer request directed to healthcare entity E3 650 is added to the entity-specific copy $P_1$, triggering the creation of an entity-specific copy $P_2$ of the aggregate healthcare record for E3 650 through a copy-on-request operation. Subsequently, one or more users at healthcare entity E3 650 may be added to the dedicated communication channel.

As shown at 652, at time t6, a user at healthcare entity E3 650 edits entity-specific copy $P_2$, e.g., by adding or modifying information in the entity-specific copy $P_2$. If the edited information is shared information to be synchronized, shown as the positive exit from decision block 655, the editing may trigger an update to the shared information in the entity-specific copy $P_0$, shown at 615 and an update to the shared information in the entity-specific copy $P_1$, shown at 635, to reflect the edits made at healthcare entity E3 650. However, if the edited information is not shared information to be synchronized, shown as the negative exit from decision block 655, no such actions are taken, as in 656.

As shown at 616, at time t7, a user at healthcare entity E1 610 edits entity-specific copy $P_0$, e.g., by adding or modifying information in the entity-specific copy $P_0$. If the edited information is shared information to be synchronized, shown as the positive exit from decision block 620, the editing may trigger an update to the shared information in the entity-specific copy $P_2$, shown at 653 and an update to the shared information in the entity-specific copy $P_1$, shown at 636, to reflect the edits made at healthcare entity E1 610. However, if the edited information is not shared information to be synchronized, shown as the negative exit from decision block 620, no such actions are taken, as in 621.

As shown at 637, at time t8, a user at healthcare entity E2 630 edits entity-specific copy $P_1$, e.g., by adding or modifying information in the entity-specific copy $P_1$. If the edited information is shared information to be synchronized, shown as the positive exit from decision block 640, the editing may trigger an update to the shared information in the entity-specific copy $P_0$, shown at 617 and an update to the shared information in the entity-specific copy $P_2$, shown at 654, to reflect the edits made at healthcare entity E2 630. However, if the edited information is not shared information to be synchronized, shown as the negative exit from decision block 640, no such actions are taken, as in 641.

Figure 7:
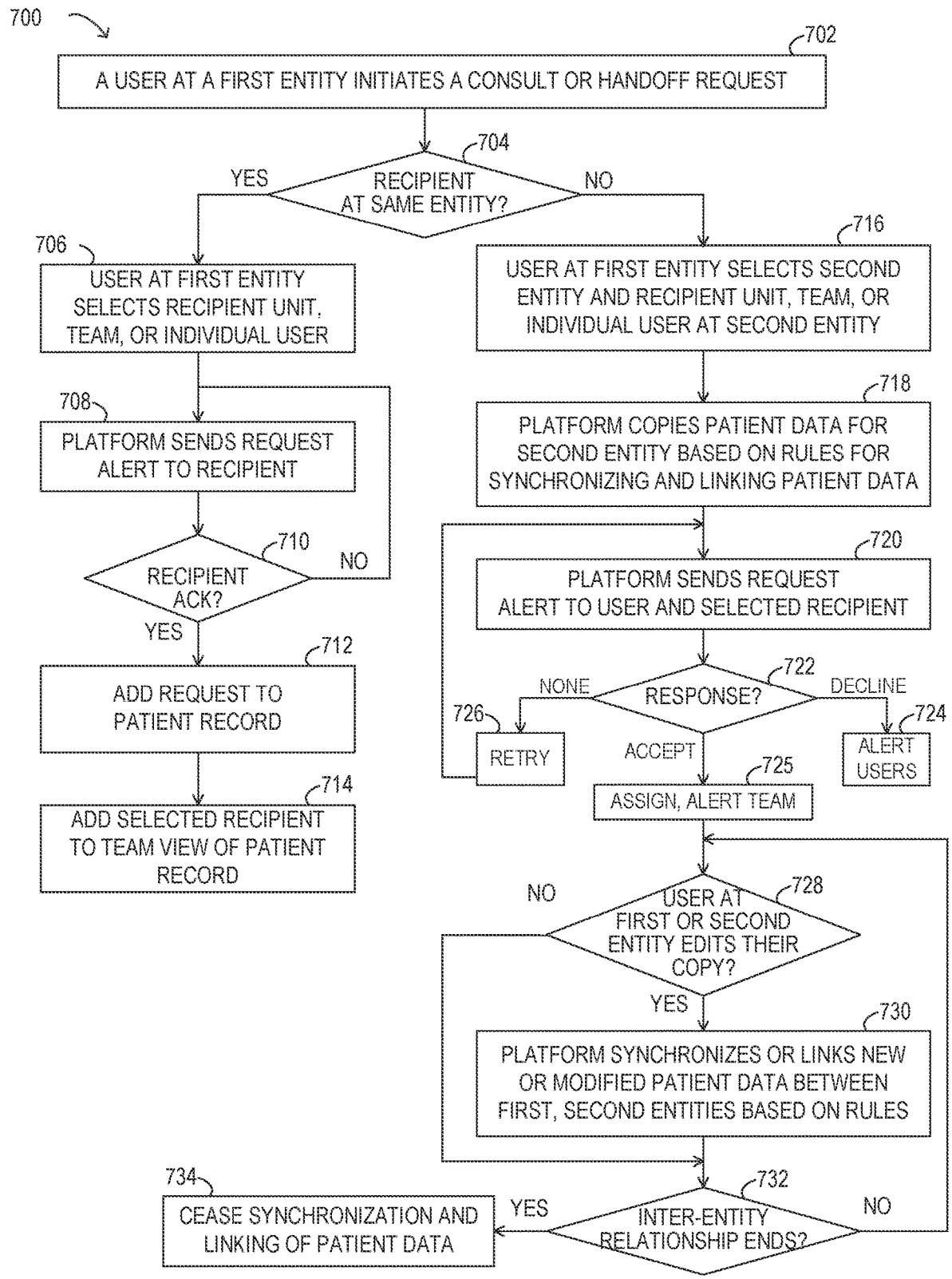
FIG. 7 is flow diagram illustrating selected elements of a method for sending alerts to selected recipients of an information sharing request, according to some embodiments.

FIG. 7 is flow diagram illustrating selected elements of an embodiment of a method 700 for sending alerts to selected recipients of an information sharing request. In various embodiments, operations of method 700 may be performed by an inter-facility communication platform, such as inter-facility communication platform 110 illustrated in FIG. 1, in conjunction with multiple client computing devices, such as client computing devices 130 illustrated in FIG. 1. Method 700 may be performed once or repeatedly to send alerts to selected recipients of various information sharing request. It is noted that certain operations described in method 700 may be optional or may be rearranged in different embodiments.

At 702, method 700 includes a user at first healthcare entity initiating a consult or handoff request on behalf of a given patient.

If, at 704, it is determined that the target recipient of the consult or handoff request is associated with, or resides at, the same healthcare entity as the user initiating the request, method 704 may continue at 706. Otherwise, the method may proceed to 716. In one example, the user may be a first responder at an EMS agency and the target recipient may be another healthcare provider at the same EMS agency. In another example, the user may be a first provider in an emergency department of a hospital and the target recipient may be a user in a different department at the same hospital. In either of these cases, no additional copy of an aggregate healthcare record for the given patient may need to be generated in response to the request.

At 706, the method may include the user at the first healthcare entity selecting a recipient unit, team, or individual user. At 708, method 700 may include the communication platform sending a request alert to the selected recipient.

If, at 710, it is determined that the recipient has not acknowledged the request alert, method 700 may return to 708, where the operation to send the request alert to the selected recipient may be repeated. In some embodiments, the operation to send the request alert to the selected recipient may be repeated up to a predefined maximum number of times before it is considered to have failed and the attempt is abandoned. If, at 710, it is determined that the recipient has acknowledged the request alert, method 700 may continue at 712, where the request is added to the aggregate healthcare record for the given patient.

At 714, the method may include adding the selected recipient to a team view of the aggregate healthcare record for the given patient.

At 716, method 700 may include the user at the first healthcare entity selecting the second healthcare entity and a recipient unit, team, or individual user at the second healthcare entity.

At 718, the method may include the communication platform copying patient data for second healthcare entity based on medical information sharing rules for synchronizing and linking patient data. For example, the communication platform may, based on the medical information sharing rules, define a copy of the aggregate healthcare record associated with the given patient for the second healthcare entity including shared data that is synchronized between healthcare entities, but not including linked data or entity-specific data for another healthcare entity.

At 720, method 700 may include the communication platform sending a request alert to the selected recipient and, in some embodiments, to the initiating user. If, at 722, there is no response to the request alert, this may trigger a retry, as in 722, including returning to 720 where the operation to send the request alert to the selected recipient may be repeated may be repeated. In some embodiments, the operation to send the request alert to the selected recipient may be repeated up to a predefined maximum number of times before it is considered to have failed and the attempt is abandoned.

If, at 722, the request is declined, the method may proceed to 724, where an alert is pushed to the first user and to the target recipient indicating that the request has been declined. For example, a consult or handoff request may be denied if the user at the first entity has selected an unsuitable or unavailable recipient for the request.

If, at 722, the request is accepted, one or more team members at the second entity may be assigned to the given patient and alerted to their assignments, as in 725, after which method 700 may proceed to 728.

If, at 728, a user of a client computing device at the first healthcare entity or at the second healthcare entity edits their copy of the aggregate healthcare record, the method may continue at 730. Otherwise, the method may proceed to 732. At 730, the method may include the communication platform synchronizing or linking new or modified patient data between the first and second healthcare entities based on the applicable medical information sharing rules.

If, at 732, an inter-entity relationship between the first and second entities remains active, method 700 may return to 728, after which the operations shown as 728 and 730 may be repeated one or more times as the aggregate healthcare record for the given patient is edited by users of client computing devices at the first or second healthcare entity.

If and when, at 732, it is determined that an inter-entity relationship between the first and second entities no longer exists, either for this patient or entity-wide, method 700 may proceed to 734, where the synchronization and linking of patient data across entity-specific copies of an aggregate healthcare record is discontinued. As illustrated in this example, one or more copies of the aggregate healthcare record for the given patient may, optionally, be deleted once the inter-entity relationship between the first and second healthcare entities no longer exists. For example, in some embodiments, once a patient handoff is complete and the given patient has been transported to a receiving facility, a first responder or a user at an EMS agency or another originating healthcare entity may withdraw from, or be removed from, the dedicated patient communication channel for the given patient. In other embodiments, no healthcare entity is removed from the dedicated patient communication channel for the given patient until the case is stopped, e.g., until the case is resolved and/or the patient is discharged.

In some embodiments, a user of a client computing device of an inter-facility communication system may be able to select multiple recipients of an information sharing request including users in the same entity and users in different entities. In this case, in response to an information sharing request, additional entity-specific copies of an aggregate healthcare record for the patient may be created only at recipient healthcare entities other than the healthcare entity that originated the request.

Figure 8:
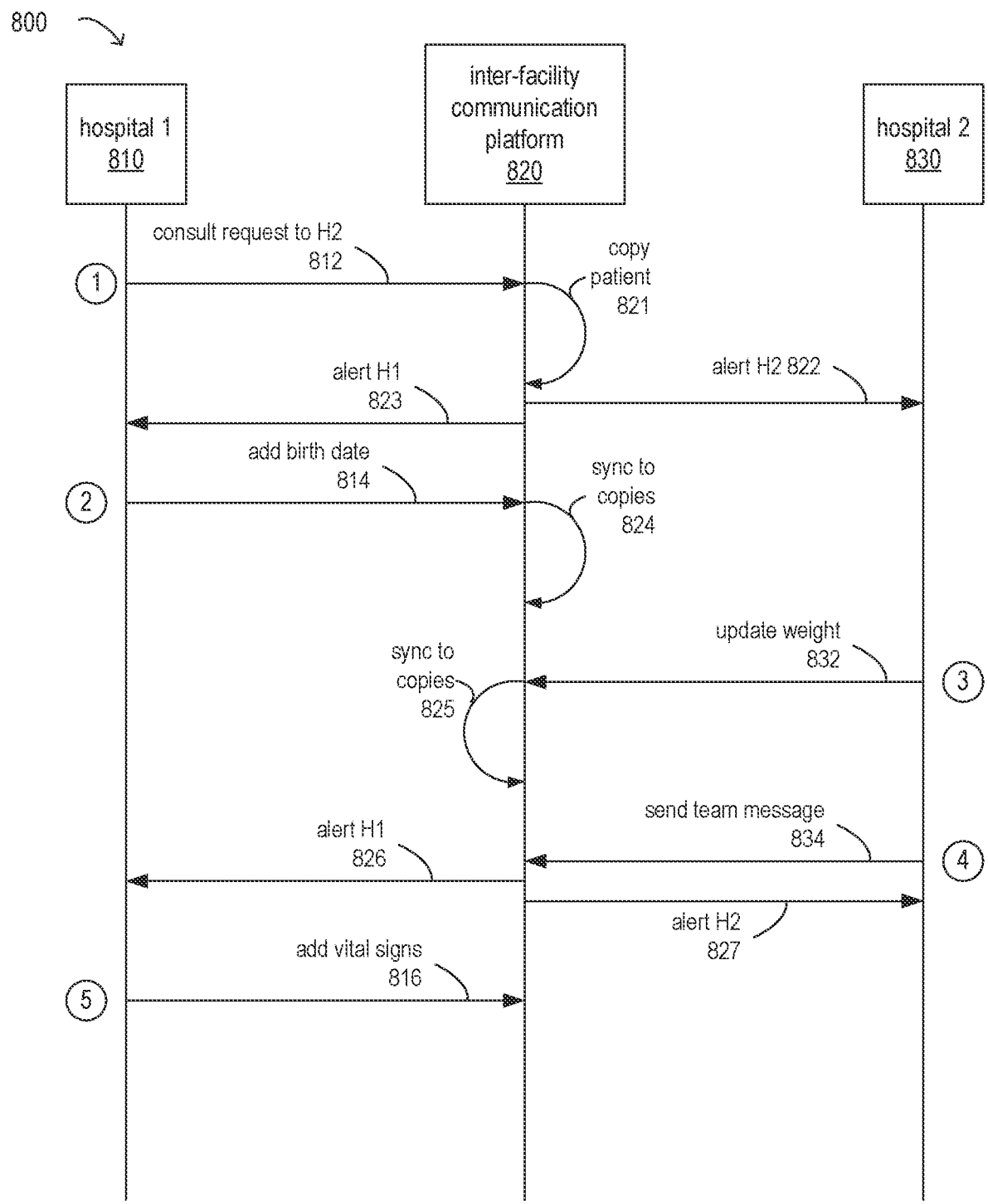
FIG. 8 is an example sequence diagram illustrating selected actions taken by an inter-facility communication platform in response to data sharing requests, according to some embodiments.

FIG. 8 is an example sequence diagram 800 illustrating selected actions taken by an inter-facility communication platform in response to information sharing requests, according to some embodiments. More specifically, sequence diagram 800 illustrates actions taken by an inter-facility communication platform 820 in response to actions taken by hospital 1 (810) or hospital 2 (830).

In the illustrated example, a first action, taken by hospital 1 (810), is the initiation of a consult request directed to hospital 2, shown as consult request 812. The consult request may be sent over a dedicated communication channel for the given patient and may be detected or received by the inter-facility communication platform 820. In response to detecting or receiving consult request 812, inter-facility communication platform 820 copies at least a portion of the patient data in the aggregate healthcare record for the given patient to create an entity-specific copy of the aggregate healthcare record for hospital 2 (830). The portion of the patient data copied to the entity-specific copy of the aggregate healthcare record for hospital 2 (830) may be dependent on medical information sharing rules such as those described herein. The inter-facility communication platform 820 then sends alerts, shown as alerts 822 and 823, to hospital 2 (830) and hospital 1 (810) indicating that hospital 2 (830) has been added to the dedicated communication channel for the given patient.

In the illustrated example, a second action, taken by hospital 1 (810), is the addition of a patient birth date in an entity-specific copy of an aggregate healthcare record for the given patient at hospital 1 (810), shown as editing action 814. In this example, a patient birth date is shared data that is synchronized between entity-specific copies of the aggregate healthcare record for the given patient. Therefore, in response to detecting editing action 814, inter-facility communication platform 820 synchronizes (at 824) the entity-specific copies of the aggregate healthcare record for other healthcare entities on the dedicated communication channel for the given patient, including the entity-specific copy of the aggregate healthcare record for hospital 2 (830), to reflect the change made at hospital 1 (810).

In the illustrated example, a third action is taken by hospital 2 (830). In this case, the action, shown as editing action 832, is the updating of a patient weight in an entity-specific copy of an aggregate healthcare record for the given patient at hospital 2 (830). In this example, patient weight data is shared data that is synchronized between entity-specific copies of the aggregate healthcare record for the given patient. Therefore, in response to detecting editing action 832, inter-facility communication platform 820 synchronizes (at 825) the entity-specific copies of the aggregate healthcare record for other healthcare entities on the dedicated communication channel for the given patient, including the entity-specific copy of the aggregate healthcare record for hospital 1 (810), to reflect the change made at hospital 2 (830).

In the illustrated embodiment, a fourth action, taken by hospital 2 (830), is the sending of a team message, shown as message 834, to one or more other healthcare entities on the dedicated communication channel for the given patient including hospital 1 (810). The message 834 may be detected or received by the inter-facility communication platform 820. In response to detecting or receiving message 834, inter-facility communication platform 820 sends alerts, shown as alerts 826 and 827, to hospital 1 (810) and hospital 2 (830) indicating that hospital 2 (834) has sent a team message over the dedicated communication channel for the given patient.

In the illustrated example, a fifth action, taken by hospital 1 (810), is the addition of patient vital signs in an entity-specific copy of an aggregate healthcare record for the given patient at hospital 1 (810), shown as editing action 816. In this example, vital sign information is linked data that is owned by hospital 1 (810) and is visible to other healthcare entities on the dedicated communication channel, rather than shared data that is synchronized between entity-specific copies of the aggregate healthcare record for the given patient. Therefore, no action is taken to synchronize copies of the aggregate healthcare record by inter-facility communication platform 820 in response to detecting editing action 816.

Figure 9:
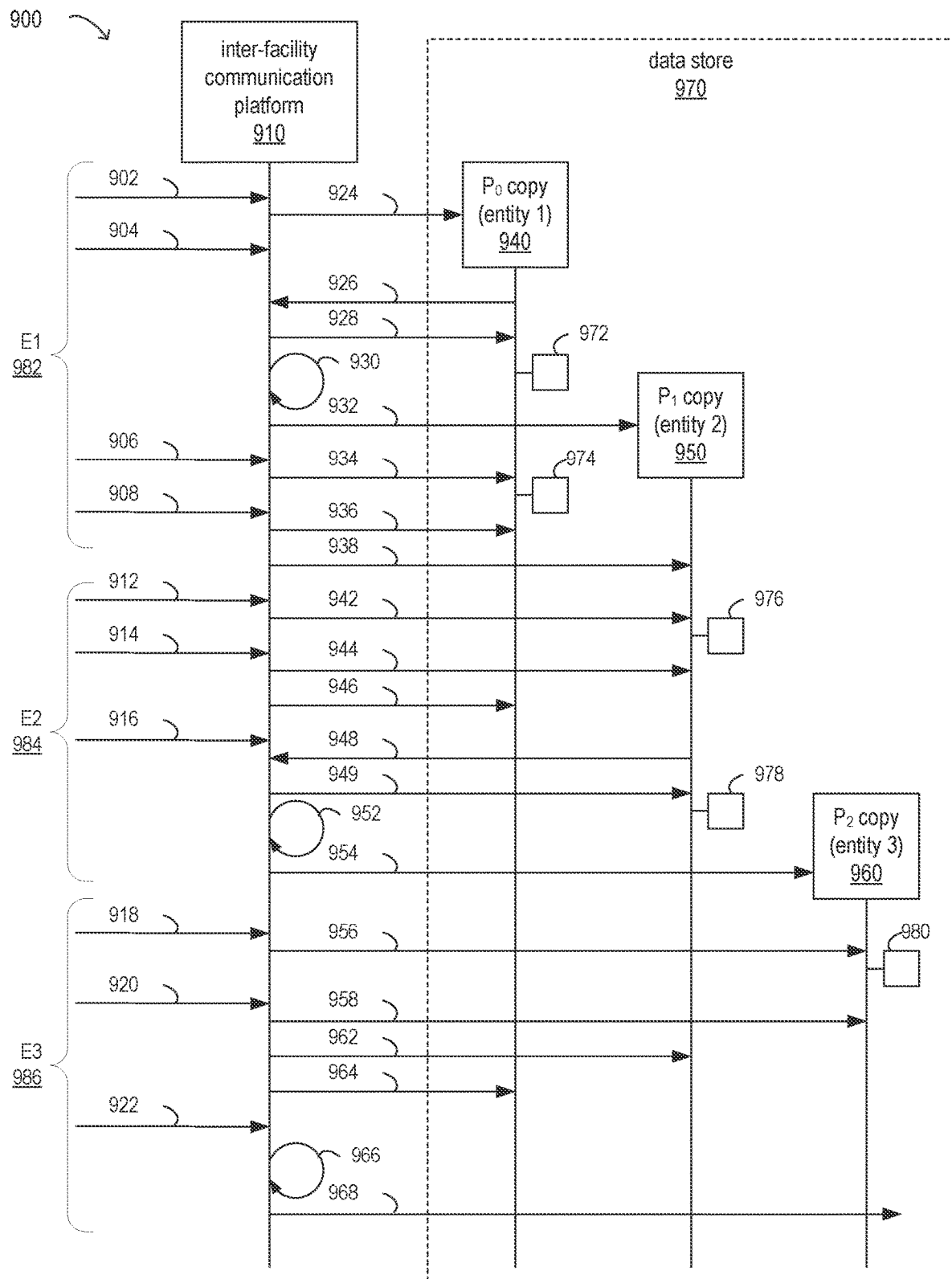
FIG. 9 is another example sequence diagram illustrating selected actions taken by an inter-facility communication platform in response to data sharing requests, according to some embodiments.

FIG. 9 is an example sequence diagram 900 illustrating selected actions taken by an inter-facility communication platform in response to information sharing requests, according to some embodiments. More specifically, sequence diagram 900 illustrates actions taken by an inter-facility communication platform 910 in response to information sharing requests and other actions taken by users at three healthcare entities, E1 (982), E2 (984), and E3 (986). In at least some cases, the actions taken by the users at the healthcare entities result a change to patient data stored on behalf of a given user in data store 970. Data store 970 may reside on inter-facility communication platform 910 hardware or may be remote storage, such as cloud-based storage, in different embodiments.

In the illustrated example, in response to a request by a user at E1 (982) to create a dedicated communication channel for a given patient, shown as request 902, platform 910 establishes a dedicated communication channel for the given patient, including creating (924) a first entity-specific copy of an aggregate healthcare record for the given patient for E1 (982) in data store 970, shown as $P_0$ (940).

In the illustrated example, in response to a request by a user at E1 (982) to transfer the given patient to E2 (984), shown as transfer request 904, platform 910 fetches (at 926) the patient data of $P_0$ (940) from data store 970, adds (at 928) data representing transfer request 904 to $P_0$ (940), and filters (at 930) the patient data of $P_0$ (940) to create (at 932) an entity-specific copy of the aggregate healthcare record for E2 (984) in data store 970, shown as $P_1$ (950). The addition of the data representing the transfer request to $P_0$ (940) is shown as data element 972. The filtering may be dependent on medical information sharing rules defining shared information, linked information, and entity-specific information in the aggregate healthcare record.

In the illustrated example, in response to a user at E1 (982) requesting (at 906) the addition of an image to $P_0$ (940), platform 910 adds (at 934) the image to $P_0$ (940) as image 974. In response to a user at E1 (982) requesting (at 908) a change to the patient's name in $P_0$ (940), platform 910 synchronizes the current entity-specific copies of the aggregate healthcare record for the given patient by updating the patient's name first, at 936, in $P_0$ (940), as requested, and then, at 938, in $P_1$ (950).

In the illustrated example, in response to a user at E2 (984) requesting (at 912) the addition of an image to $P_1$ (950), platform 910 adds (at 942) the image to $P_1$ (950) as image 976. In response to a user at E2 (984) requesting (at 916) a change to the patient's age in $P_1$ (950), platform 910 synchronizes the current entity-specific copies of the aggregate healthcare record for the given patient by updating the patient's age first, at 944, in $P_1$ (950), as requested, and then, at 946, in $P_0$ (940).

In the illustrated example, in response to a request by a user at E2 (984) to transfer the given patient to E3 (986), shown as transfer request 916, platform 910 fetches (at 948) the patient data of $P_1$ (950) from data store 970, adds (at 949) data representing transfer request 916 to $P_1$ (950), and filters (at 952) the patient data of $P_1$ (950) to create (at 954) an entity-specific copy of the aggregate healthcare record for E3 (986) in data store 970, shown as $P_2$ (960). The addition of the data representing the transfer request to $P_1$ (950) is shown as data element 978. The filtering may be dependent on medical information sharing rules defining shared information, linked information, and entity-specific information in the aggregate healthcare record.

In the illustrated example, in response to a user at E3 (986) requesting (at 918) the addition of an image to $P_2$ (960), platform 910 adds (at 956) the image to $P_2$ (960) as image 980. In response to a user at E3 (986) requesting (at 920) a change to the patient's birth date in $P_2$ (960), platform 910 synchronizes the current entity-specific copies of the aggregate healthcare record for the given patient by updating the patient's birth date first, at 958, in $P_1$ (950), as requested, then, at 962, in $P_1$ (950) and finally, at 964, in $P_0$ (940).

In the illustrated example, in response to a user at E3 (986) requesting (at 922) a change to door time data in $P_2$ (960), platform 910 determines (at 966) that this information should not be synchronized across the entity-specific copies of the aggregate healthcare record for the given patient, and then updates (at 968) the door time data in $P_2$ (960) only. The determination may be based on medical information sharing rules defining shared information, linked information, and entity-specific information in the aggregate healthcare record.

In at least some embodiments, the systems described herein may be configured to present patient data in an aggregate healthcare record in any of several different views. For example, a user may be able to view, on a client computing device, aggregations of data items by type, e.g., as library of audio clips including the time and the healthcare entity at which each was recorded and an identifier of the user who recorded the audio clip, a list of all messages exchanged on the patient communication channel including time and the healthcare entity at which each was sent and identifiers of the users who sent and received each message, or an image gallery of all uploaded images attached to the aggregate healthcare record including the time and the healthcare entity at which each was uploaded.

In at least some embodiments, a user may be able to view, on a client computing device, any and all shared and linked data items in an aggregate healthcare record for a given patient, regardless of the respective healthcare entities that own each of them, in chronological order for different information sharing requests that were initiated and for actions that were taken by the inter-facility communication platform in response.

Figure 10A:
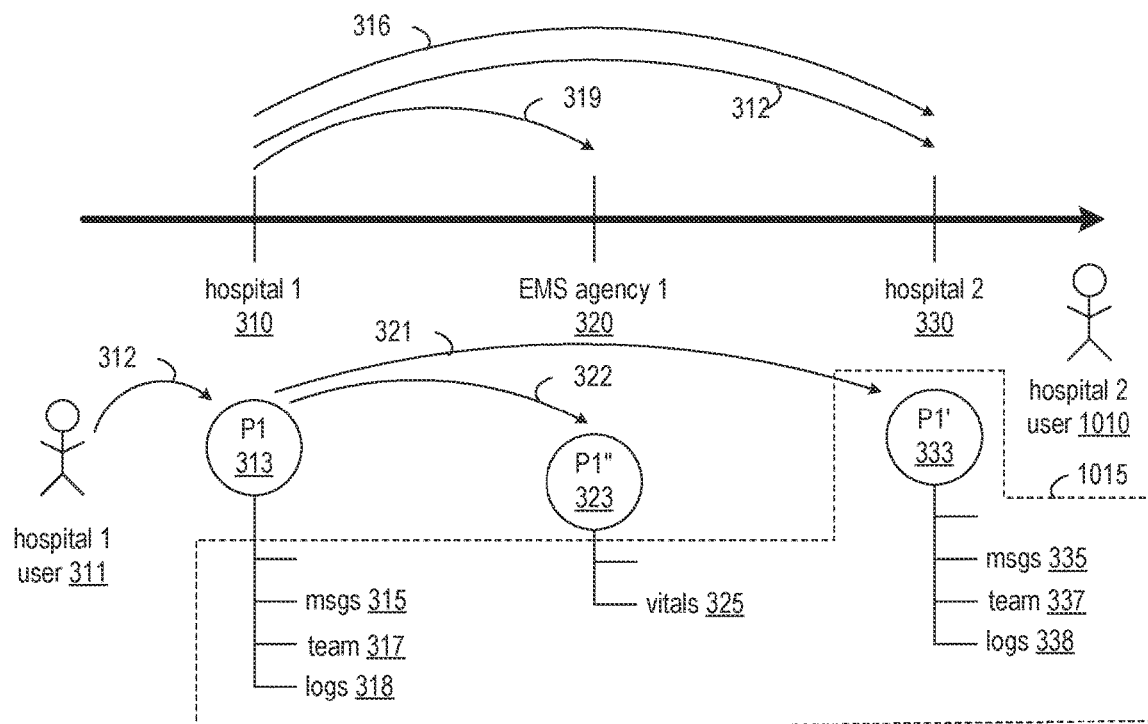
FIGS. 10A through 10D illustrate elements of an aggregate record are provided for display at different entities, according to some embodiments.

FIGS. 10A through 10D illustrate which elements of an aggregate healthcare record associated with a given patient are visible by users at different healthcare entities, according to some embodiments. For example, FIG. 10A illustrates a patient data view from the perspective of a hospital user 2 (1010) following the scenario illustrated in FIGS. 3A through 3D. In this example, hospital user 2 (1010) is able view all of the linked patient data shown within the dashed border 1015, as well as the shared data included in the entity-specific copy of the aggregate healthcare record owned by hospital 2 (330), shown as P1' (333).

Figure 10B:
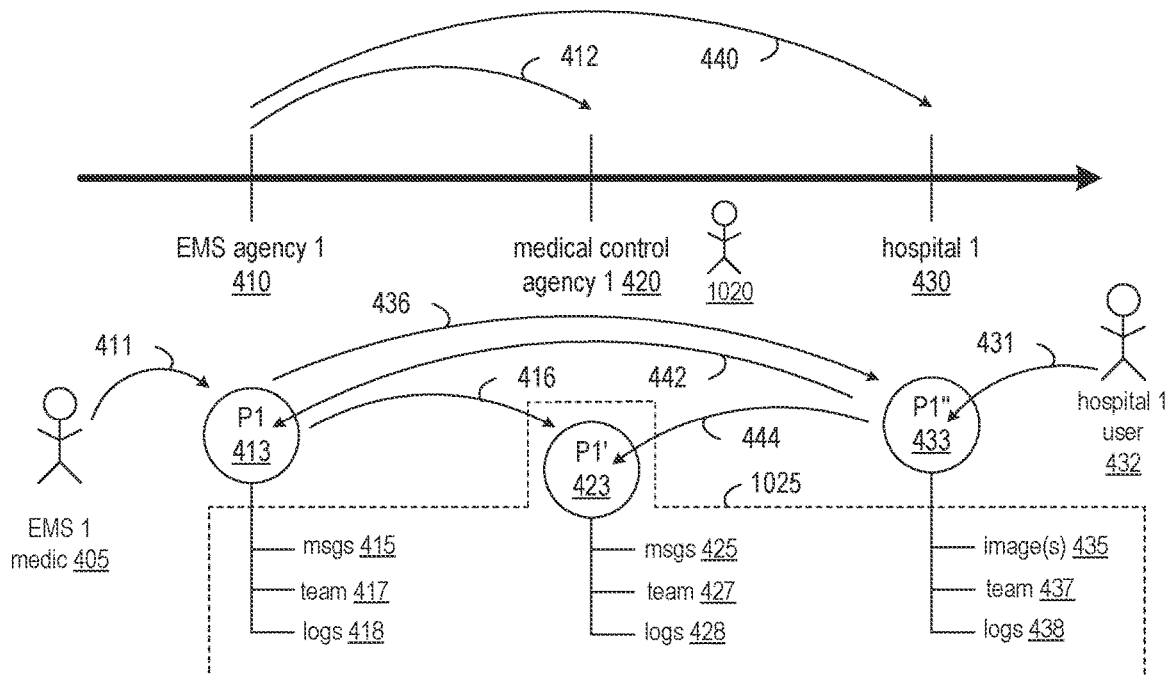

In another example, FIG. 10B illustrates a patient data view from the perspective of a user 1020 at medical control agency 1 (420) following the scenario illustrated in FIGS. 4A through 4F. In this example, user 1020 is able view all of the linked patient data shown within the dashed border 1025, as well as the shared data included in the entity-specific copy of the aggregate healthcare record owned by medical control agency 1 (420), shown as P1' (423).

Figure 10C:
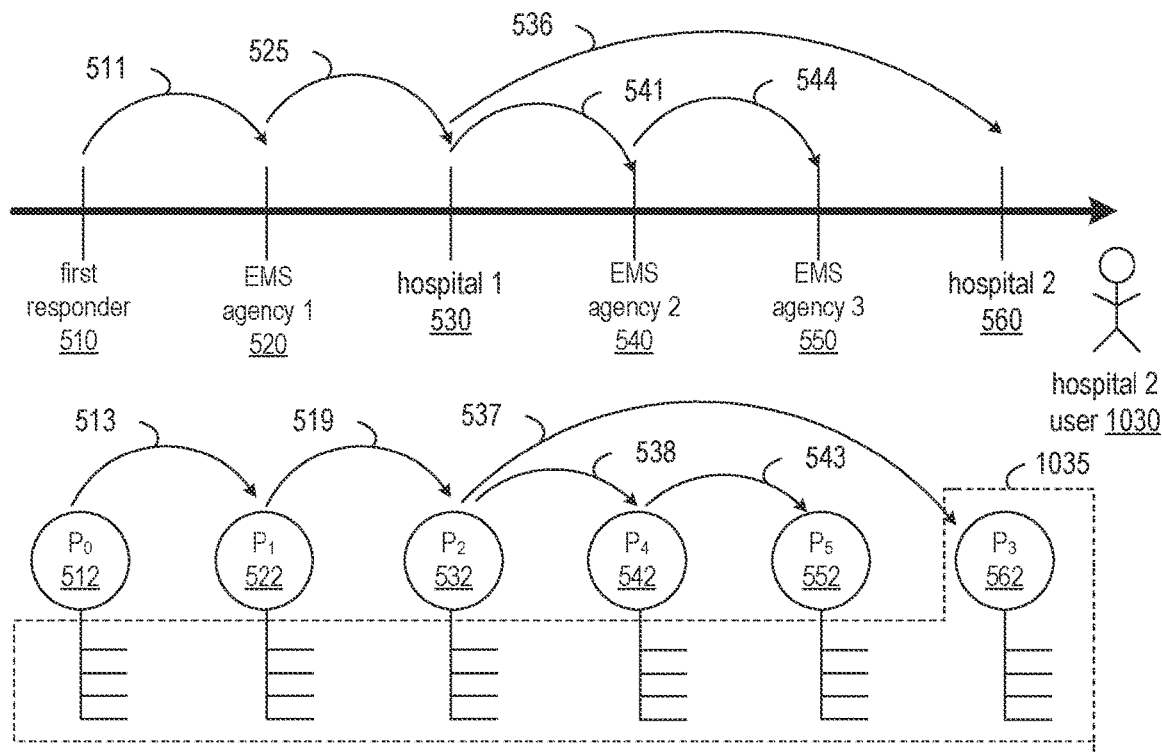

Similarly, FIG. 10C illustrates a patient data view from the perspective of a hospital user 2 (1030) following the scenario illustrated in FIGS. 5A through 5H. In this example, a hospital user 2 (1030) is able view all of the linked patient data shown within the dashed border 1035, as well as the shared data included in the entity-specific copy of the aggregate healthcare record owned by hospital 1 (560), shown as $P_3$ (562).

Figure 10D:
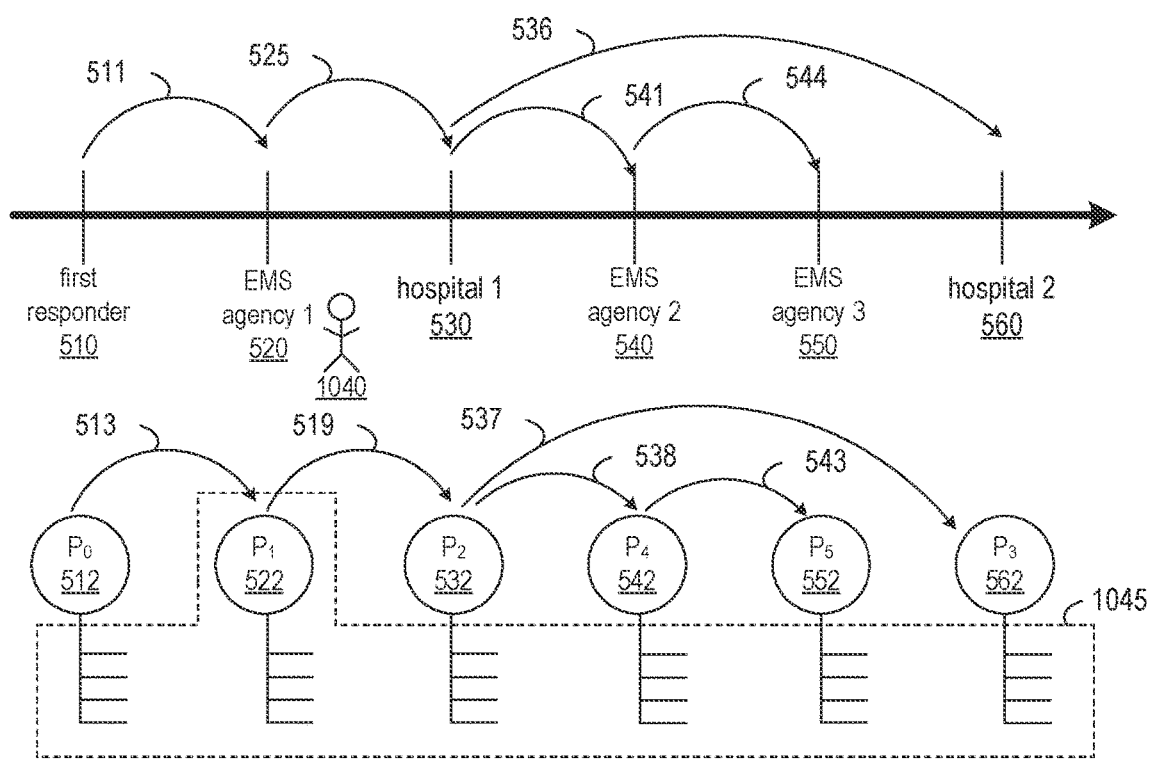

Finally, FIG. 10D illustrates a patient data view from the perspective of a user (1040) at EMS agency 1 (520) following the scenario illustrated in FIGS. 5A through 5H. In this example, user 1040 is able view all of the linked patient data shown within the dashed border 1045, as well as the shared data included in the entity-specific copy of the aggregate healthcare record owned by EMS agency 1 (520), shown as $P_1$ (522).

Note that, in some embodiments, all of the entity-owned information shown in the figures herein may be visible to users of client computing devices at the other entities as linked information, in other embodiments, at least some of the entity-owned information may be private information that is neither synchronized between the healthcare entities nor visible to users at a healthcare entity other than the healthcare entity that owns the entity-specific information.

In some embodiments, the techniques described herein for exchanging medical information between healthcare entities using dedicated patient communication channels may be implemented by a service provider and provided as a service to healthcare entities, such as collections of healthcare entities that have established inter-entity relationships with each other. In other embodiments, the techniques described herein may be provided as a computer program product, stored on a computer-readable medium, for implementing any of the methods described herein. For example, a computer program product may store instructions that, when executed by one or more processors of inter-facility communication platform hardware or on respective client computing devices at multiple healthcare entities, cause the processors to perform the methods described herein. In some embodiments, the techniques described herein may be provided as a web-based application, such as for an inter-facility communication platform administrator.

Figure 11:
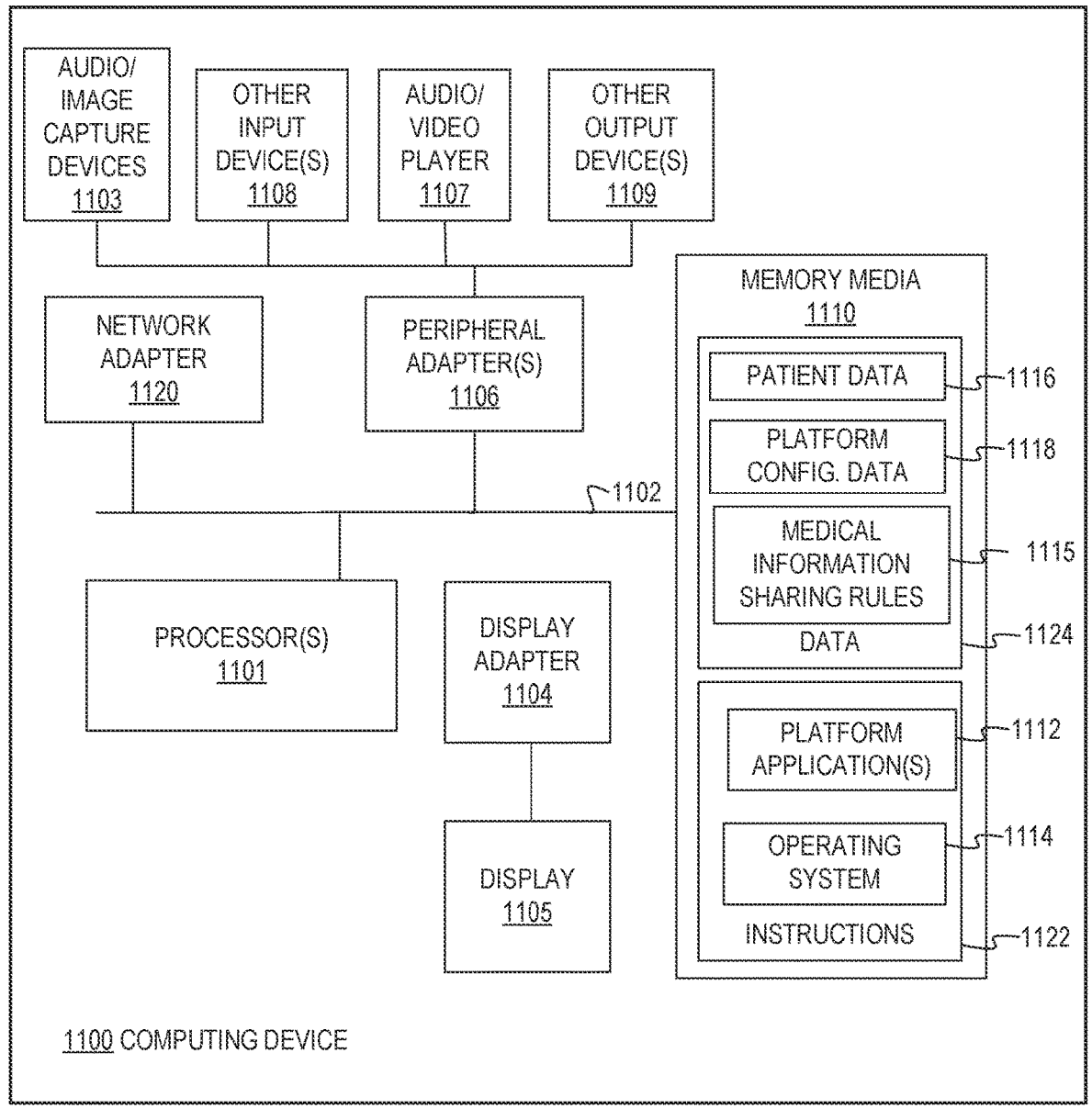
FIG. 11 is a block diagram illustrating selected elements of an embodiment of a computing device for performing any of the methods described herein for exchanging medical information between healthcare entities using dedicated patient communication channels.

FIG. 11 is a block diagram illustrating selected elements of an embodiment of a computing device 1100 for performing any of the methods described herein for exchanging medical information between healthcare entities using dedicated patient communication channels. For example, computing device 1100 may represent a computing device that implements the functionality of any of the inter-facility communication platforms or client computing devices described herein. Computing device 1100 may be a mainframe computer, a desktop computer, or a portable computing device, such as a notebook computer, media player, personal data assistant, digital camera, cellular phone, smart phone, or tablet computer. In the embodiment depicted in FIG. 11, computing device 1100 includes one or more processors 1101 coupled via shared bus 1102 to processor accessible storage media collectively identified as memory media 1110.

Computing device 1100, as depicted in FIG. 11, further includes network adapter 1120 that interfaces computing device 1100 to a network (not shown in FIG. 11) though which an inter-facility communication platform and various instances of a client computing device communicate with other to exchange medical information over a dedicated patient communication channel, as described herein. Computing device 1100, as depicted in FIG. 11, may include one or more peripheral adapters 1106, each of which may provide connectivity for the use of one or more audio or image capture devices 1103, such as a camera, a video camera, or a voice recorder, other input devices 1108, an audio or video player 1107, and/or other output devices 1109. Input devices 1108 may represent any of various devices for user input, such as a keyboard, a mouse, a microphone, a touchpad, or a touchscreen. In some embodiments, input devices 1108 may include medical devices that are integrated with, or communicatively coupled to, computing device 1100 to provide data or images that can be attached to an aggregate healthcare record for a given patient. In some embodiments, input devices 1108 may include monitoring devices that provide data indicating heart rate, respiration, blood oxygen levels, or blood pressure, for example. In other embodiments, input devices 1108 may include medical scanning or imaging devices that provide images to be attached to an aggregate healthcare record for a given patient. Output devices 1109 may represent any of various devices for providing signals or indications to a user, such as one or more speakers for generating audio signals. Audio/video player 1107 and/or audio/image camera 1103 might or might not be coupled to or integrated with display 1105, in different embodiments. In some embodiments, one of peripheral adapters 1106 may include a video camera interface or driver, or a driver for another type of input/output device, including a driver for a voice recorder or one or more GUI drivers for capturing inputs from users.

Computing device 1100 is shown in FIG. 11 including display adapter 1104 and further includes a display device or, more simply, a display 1105. Display adapter 1104 may interface shared bus 1102, or another bus, with an output port for one or more displays, such as display 1105. Display 1105 may comply with a display standard for computer monitors and/or television displays. Standards for computer monitors include analog standards such as video graphics array (VGA), extended graphics array (XGA), etc., or digital standards such as digital visual interface (DVI) and high definition multimedia interface (HDMI), among others. A television display may comply with standards such as National Television System Committee (NTSC), Phase Alternating Line (PAL), or another suitable standard. Display 1105 may include an output device 1109, such as one or more integrated speakers to play audio content, or may include an input device 1103 or 1108, such as a microphone, voice recorder, or video camera.

Memory media 1110 may encompass persistent and volatile media, fixed and removable media, and magnetic and semiconductor media, in various embodiments. Memory media 1110 is operable to store instructions, data, or both. Memory media 1110 is shown as a non-transitory computer readable memory media storing instructions 1122, which may represent one or more sets of instructions and data structures embodying or utilized by any one or more of the methods and/or operations described herein. It is noted that instructions 1122 may also reside, completely or at least partially, within processor 1101 during execution thereof by computing device 1100 (not shown in FIG. 11). It is further noted that processor 1101 may be configured to receive instructions 1122 from memory media 1110 via shared bus 1102. Memory media 1110 as shown includes sets or sequences of instructions 1122, namely, operating system 1114, and one or more platform applications 1112, which may perform any of the methods described herein for inter-facility exchange of medical information using dedicated patient communication channels. For example, in some embodiments, platform applications 1112 may include an inter-facility communication platform application configured to manage communications for exchanging medical information between multiple healthcare entities on behalf of a given patient. In some embodiments, platform applications 1112 may include a client application configured to operate on a client computing device of a user at a healthcare entity and to interact with an inter-facility communication platform to exchange medical information with client computing devices of users at other healthcare entities. In some embodiments, a user at a healthcare entity may log into, and operate, a platform application 1112 as a healthcare provider, such as a first responder, an emergency medical technician (EMT), a doctor, a nurse, or a lab technician, for example, who provides healthcare services to a given patient or as an administrator authorized to add or modify configuration information, such as platform configuration data 1118 and/or medical information sharing rules 1115.

Memory media 1110 is also shown storing data 1124, including patient data 1116, platform configuration data 1118, and medical information sharing rules 1115. In various embodiments, patient data 1116 may include multiple entity-specific copies of an aggregate healthcare record for a given patient. As described herein, in some embodiments, the aggregate healthcare record for a given patient may be stored in a relational database in which multiple entity-specific subsets of the patient data in the aggregate healthcare record are defined. In some embodiments, platform configuration data 1118 may include data identifying healthcare entities with which a healthcare entity at which a user operates computing device 1100 has inter-entity relationships. In some embodiments, medical information sharing rules 1115 may include rules defining shared information that is automatically synchronized between healthcare entities, linked information that is not synchronized between healthcare entities but is visible to users at multiple healthcare entities, and entity-specific information that is neither synchronized between the healthcare entities nor visible to users at a healthcare entity other than a healthcare entity that owns the entity-specific information.

In various embodiments, a client computing device being operated by a user at a particular entity might or might not store the entity-specific copy of the aggregate healthcare record defined for the particular entity locally from time to time, e.g., temporarily while a user is actively using the client computing device to add or modify information in the aggregate healthcare record.

The methods and systems disclosed herein for exchanging medical information between healthcare entities using dedicated patient communication channels may provide technical and economic benefits to the healthcare entities at which they are deployed. For example, by providing real-time automated sharing of medical information associated with a given patient across multiple healthcare entities involved in the given patient's care using the dedicated patient communication channels, rule-based information sharing, synchronization techniques, and push notifications described herein, rather than having to wait for a slower exchange of information between healthcare entities or performing redundant tests or treatments due to a lack of visibility into patient data captured while the patient was at another healthcare entity, significant amounts of time may be cut off a typical cycle of consulting, transfer, and treatment for patients with certain conditions. This may improve resource utilization at a receiving facility, in some cases. In some cases, by shaving an hour or more off the typical cycle time using these techniques, e.g., following a stroke, patient outcomes and/or survival rates may be significantly improved.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system for multiplexing of data between entities, comprising:
   an inter-facility communication platform;
   a data store comprising an aggregate record associated with a particular individual;
   a rules data store comprising sharing rules defining:
      shared data in the aggregate record that is synchronized between a plurality of entities when added or modified at one of the plurality of entities;
      linked data in the aggregate record that is i) nonsynchronous between the plurality of entities, and ii) provided for display at the plurality of entities independent of the one of the plurality of entities at which the linked data was added or modified in the aggregate record; and
      entity-specific data that is i) nonsynchronous between the plurality of entities and ii) provided for display only at the entity that is associated with the entity-specific data;
   wherein the inter-facility communication platform is configured to:
   i) establish a communication channel over which the plurality of entities exchange data associated with the particular individual;
   ii) detect a first request from a first client computing device at a first entity of the plurality of entities to share data associated with the particular individual with a second entity of the plurality of entities over the communication channel;
   iii) receive an indication from a second client computing device at the second entity that the first requested is accepted;
   iv) in response to the first request being accepted, share a first portion of the aggregate record associated with the particular individual with the second client computing device at the second entity, wherein the first portion of the aggregate record shared is dependent on the data sharing rules;

v) detect a second request from the first client computing device at the first entity to share data associated with the particular individual with a third entity of the plurality of entities over the communication channel;

vi) receive an indication from a third client computing device at the third entity that the second requested is accepted; and vii) in response to the second request being accepted, share a second portion of the aggregate record associated with the particular individual with the third client computing device at the third entity.

2. The system of claim 1, wherein the second portion of the aggregate record shared is dependent on the data sharing rules.

3. The system of claim 1, wherein the aggregate record further includes:

demographic data for the particular individual;

entity-owned data associated with the particular individual; and data representing information sharing requests exchanged between the plurality of entities associated with the particular individual.

4. The system of claim 1, wherein:

the second entity is a receiving facility;

the third entity is a transporting agency;

the first request is a consult request;

the second request is a handoff type; and the communication platform is further configured to detect, subsequent to detecting the first request and prior to detecting the second request, a third request from the first client computing device at the first entity to the receiving facility, the third request being a handoff request.

5. The system of claim 1, wherein:

to share the first portion of the aggregate record with the second client computing device at the second entity, the communication platform is configured to define an entity-specific copy of the aggregate record for the second entity including the shared data defined by the data sharing rules and independent of linked data added or modified by an entity other than the second entity or entity-specific data associated with an entity other than the second entity; and to share the second portion of the aggregate record with the third client computing device at the third entity, the communication platform is configured to define an entity-specific copy of the aggregate record for the third entity including the shared data defined by the data sharing rules and independent of linked data added or modified by an entity other than the third entity or entity-specific data associated with an entity other than the third entity.

6. The system of claim 1, wherein:

the shared information in the aggregate record includes demographic data associated with the particular individual; and the communication platform is further configured to automatically synchronize the demographic data in the aggregate record across all entity-specific copies of the aggregate record responsive to detecting that demographic data has been added or modified in an entity-specific copy of the aggregate record for a given entity.

7. The system of claim 1, wherein the communication platform is further configured to:

push an alert notification to the plurality of entities responsive to detecting that linked data has been added or modified in the aggregate record.

8. A computer-implemented method for multiplexing of data between entities, comprising:

establishing a communication channel over which a plurality of entities exchange data associated with a particular individual;

initiating, by a first client computing device at a first entity of the plurality of entities, a first request to share data associated with the particular individual with a second client computing device at a second entity of the plurality of entities;

initiating, by the first client computing device at the first entity, a second request to share data associated with the particular individual with a third client computing device at a third entity of the plurality of entities;

receiving an indication from the second client computing device at the second entity that the first requested is accepted;

receiving an indication from the third client computing device at the third entity that the second requested is accepted;

sharing, in response to the first request being accepted, a first portion of an aggregate record associated with the particular individual with the second client computing device at the second entity; and sharing, in response to the second request being accepted, a second portion of the aggregate record with the particular individual with the third client computing device at the third entity, wherein the first portion and the second portion of the aggregate record shared is dependent on data sharing rules defining:

shared data in the aggregate record that is synchronized between the plurality of entities when added or modified by a client computing device at one of the plurality of entities;

linked data in the aggregate record that is i) nonsynchronous between the plurality of entities, and ii) provided for display at the plurality of entities independent of the one of the plurality of entities at which the linked data was added or modified in the aggregate record; and entity-specific data that is i) nonsynchronous between the plurality of entities and ii) provided for display only at the entity that is associated with the entity-specific data.

9. The computer-implemented method of claim 8, wherein the second portion of the aggregate record shared is dependent on the data sharing rules.

10. The computer-implemented method of claim 8, wherein:

the second entity is a receiving facility;

the third entity is a transporting agency;

the first request is a consult request;

the second request is a handoff request; and the method further comprises detecting, subsequent to detecting the first request and prior to detecting the second request, a third request from the first client computing device at the first entity to the receiving facility, the third request being a handoff request.

11. The computer-implemented method of claim 8, wherein:
- sharing the first portion of the aggregate record with the second client computing device at the second entity comprises defining an entity-specific copy of the aggregate record for the second entity including the shared data defined by the data sharing rules and independent of linked data added or modified by an entity other than the second entity or entity-specific data associated with an entity other than the second entity; and
- sharing the second portion of the aggregate record with the third client computing device at the third entity comprises defining an entity-specific copy of the aggregate record for the third entity including the shared data defined by the data sharing rules and independent of linked data added or modified by an entity other than the third entity or entity-specific data associated with an entity other than the third entity.

12. The computer-implemented method of claim 8, wherein:
- the shared information in the aggregate record includes demographic data associated with the particular individual; and
- the computer-implemented method further comprises automatically synchronizing the demographic data in the aggregate record across all entity-specific copies of the aggregate record responsive to detecting that demographic data has been added or modified in an entity-specific copy of the aggregate record for a given entity.

13. The computer-implemented method of claim 8, further comprising:
- pushing an alert notification to the plurality of entities in response to detecting that linked data has been added or modified in the aggregate record.

14. Non-transitory computer readable memory media storing instructions executable by one or more processors for:
- establishing a communication channel over which a plurality of entities exchange data associated with a particular individual;
- initiating, by a first client computing device at a first entity of the plurality of entities, a first request to share data associated with the particular individual with a second client computing device at a second entity of the plurality of entities;
- initiating, by the first client computing device at the first entity, a second request to share data associated with the particular individual with a third client computing device at a third entity of the plurality of entities;
- receiving an indication from the second client computing device at the second entity that the first requested is accepted;
- receiving an indication from the third client computing device at the third entity that the second requested is accepted;
- sharing, in response to the first request being accepted, a first portion of an aggregate record associated with the particular individual with the second client computing device at the second entity; and
- sharing, in response to the second request being accepted, a second portion of the aggregate record with the particular individual with the third client computing device at the third entity,
- wherein the first portion and the second portion of the aggregate record shared is dependent on data sharing rules defining:
  - shared data in the aggregate record that is synchronized between the plurality of entities when added or modified by a client computing device at one of the plurality of entities;
  - linked data in the aggregate record that is i) nonsynchronous between the plurality of entities, and ii) provided for display at the plurality of entities independent of the one of the plurality of entities at which the linked data was added or modified in the aggregate record; and
  - entity-specific data that is i) nonsynchronous between the plurality of entities and ii) provided for display only at the entity that is associated with the entity-specific data.

15. The non-transitory computer readable memory media of claim 14, wherein the second portion of the aggregate record shared is dependent on the data sharing rules.

16. The non-transitory computer readable memory media of claim 14, wherein:
- sharing the first portion of the aggregate record with the second client computing device at the second entity comprises defining an entity-specific copy of the aggregate record for the second entity including the shared data defined by the data sharing rules and independent of linked data added or modified by an entity other than the second entity or entity-specific data associated with an entity other than the second entity; and
- sharing the second portion of the aggregate record with the third client computing device at the third entity comprises defining an entity-specific copy of the aggregate record for the third entity including the shared data defined by the data sharing rules and independent of linked data added or modified by an entity other than the third entity or entity-specific data associated with an entity other than the third entity.

17. The non-transitory computer readable memory media of claim 14, wherein:
- the shared information in the aggregate record includes demographic data associated with the particular individual; and
- the instructions further comprising automatically synchronizing the demographic data in the aggregate record across all entity-specific copies of the aggregate record responsive to detecting that demographic data has been added or modified in an entity-specific copy of the aggregate record for a given entity.

* * * * *